United States Patent
Terry et al.

(10) Patent No.: US 7,623,053 B2
(45) Date of Patent: Nov. 24, 2009

(54) IMPLANTABLE MEDICAL DEVICE WITH LOW POWER DELTA-SIGMA ANALOG-TO-DIGITAL CONVERTER

(75) Inventors: Michael B. Terry, Camas, WA (US);
Michael W. Heinks, New Brighton, MN (US); Joel A. Anderson, Brooklyn Park, MN (US); Mark A. Frigaard, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 5 days.

(21) Appl. No.: 11/861,920

(22) Filed: Sep. 26, 2007

(65) Prior Publication Data
US 2009/0079606 A1    Mar. 26, 2009

(51) Int. Cl.
*H03M 1/66* (2006.01)
(52) U.S. Cl. ........................... 341/143; 341/155
(58) Field of Classification Search ................... 341/143
See application file for complete search history.

(56) References Cited

U.S. PATENT DOCUMENTS

| | | | |
|---|---|---|---|
| 3,130,373 A | | 4/1964 | Braymer |
| 3,273,141 A | | 9/1966 | Hackett |
| 4,177,819 A | | 12/1979 | Kofsky et al. |
| 4,188,586 A | | 2/1980 | Egami |
| 4,466,440 A | | 8/1984 | Money et al. |
| 4,933,642 A | | 6/1990 | Lee |
| 4,990,914 A | * | 2/1991 | Giancarlo ................. 341/143 |
| 5,039,989 A | | 8/1991 | Welland et al. |
| 5,061,593 A | | 10/1991 | Yoerger et al. |
| 5,068,659 A | | 11/1991 | Sakaguchi |
| 5,068,660 A | | 11/1991 | Swanson et al. |

(Continued)

FOREIGN PATENT DOCUMENTS

EP     0 354 060      2/1990

(Continued)

OTHER PUBLICATIONS

U.S. Appl. No. 11/861,945, filed Sep. 26, 2007 entitled "Detecting Overloading of an Analog-to-Digital Converter of an Implantable Medical Device".

(Continued)

*Primary Examiner*—Khai M Nguyen
(74) *Attorney, Agent, or Firm*—Michael C. Soldner; Michael J. Ostrom

(57) ABSTRACT

In general, this disclosure describes techniques for reducing power consumption within an implantable medical device (IMD). An IMD implanted within a patient may have finite power resources that are intended to last several years. To promote device longevity, sensing and therapy circuits of the IMD are designed to incorporate an analog-to-digital converter (ADC) that provides relatively high resolution output at a relatively low operation frequency, and does so with relatively low power consumption. An ADC designed in accordance with the techniques described herein utilizes a quantizer that has a lower resolution than a digital-to-analog converter (DAC) used for negative feedback. Such a configuration provides the benefits of higher resolution DAC feedback without having the use high oversampling ratios that result in high power consumption. Also, the techniques avoid the use of, and the associated high power consumption of, a high resolution flash ADC, within the sigma delta loop.

25 Claims, 8 Drawing Sheets

U.S. PATENT DOCUMENTS

| | | | |
|---|---|---|---|
| 5,113,143 A | 5/1992 | Wei | |
| 5,179,947 A | 1/1993 | Meyerson et al. | |
| 5,208,597 A | 5/1993 | Early et al. | |
| 5,311,876 A | 5/1994 | Olsen et al. | |
| 5,329,281 A * | 7/1994 | Baumgartner et al. | 341/139 |
| 5,369,309 A | 11/1994 | Bacrania et al. | |
| 5,392,042 A | 2/1995 | Pellon | |
| 5,477,481 A | 12/1995 | Kerth | |
| 5,606,320 A | 2/1997 | Kleks | |
| 5,647,379 A | 7/1997 | Meltzer | |
| 5,663,680 A | 9/1997 | Nordeng | |
| 5,697,958 A | 12/1997 | Paul et al. | |
| 5,742,246 A | 4/1998 | Kuo et al. | |
| 5,766,227 A | 6/1998 | Nappholz et al. | |
| 5,928,272 A | 7/1999 | Adkins et al. | |
| 6,061,593 A | 5/2000 | Fischell et al. | |
| 6,064,257 A | 5/2000 | Sauer | |
| 6,064,326 A | 5/2000 | Krone et al. | |
| 6,100,834 A | 8/2000 | Lewyn | |
| 6,130,578 A | 10/2000 | Tang | |
| 6,184,811 B1 | 2/2001 | Nagari et al. | |
| 6,262,626 B1 | 7/2001 | Bakker et al. | |
| 6,354,299 B1 | 3/2002 | Fischell et al. | |
| 6,360,123 B1 | 3/2002 | Kimchi et al. | |
| 6,362,763 B1 | 3/2002 | Wang | |
| 6,389,315 B1 | 5/2002 | Schu et al. | |
| 6,456,159 B1 | 9/2002 | Brewer | |
| 6,535,153 B1 | 3/2003 | Zierhofer | |
| 6,556,859 B1 * | 4/2003 | Wohlgemuth et al. | 600/509 |
| 6,567,025 B2 | 5/2003 | Schreier et al. | |
| 6,584,157 B1 | 6/2003 | Van Der Zwan et al. | |
| 6,584,351 B1 | 6/2003 | Ekwall | |
| 6,617,838 B1 | 9/2003 | Miranda et al. | |
| 6,625,436 B1 | 9/2003 | Tolson et al. | |
| 6,700,520 B1 | 3/2004 | Miller | |
| 6,707,409 B1 | 3/2004 | Ignjatovic et al. | |
| 6,760,623 B2 | 7/2004 | Stahmann et al. | |
| 6,810,285 B2 | 10/2004 | Pless et al. | |
| 6,924,760 B1 | 8/2005 | McLeod et al. | |
| 6,999,014 B2 | 2/2006 | Oliaei et al. | |
| 7,006,872 B2 | 2/2006 | Gielen et al. | |
| 7,015,853 B1 | 3/2006 | Wolff et al. | |
| 7,049,990 B2 | 5/2006 | Ranganathan | |
| 7,053,807 B1 | 5/2006 | Gaalaas | |
| 7,061,416 B2 | 6/2006 | Nagai | |
| 7,079,061 B2 * | 7/2006 | Schuurmans | 341/143 |
| 7,098,823 B2 | 8/2006 | O'Dowd et al. | |
| 7,098,827 B2 | 8/2006 | Motz | |
| 7,102,558 B2 | 9/2006 | Deval | |
| 7,129,875 B1 | 10/2006 | Altun et al. | |
| 7,142,142 B2 | 11/2006 | Petersen et al. | |
| 7,142,143 B2 | 11/2006 | Draxelmayr | |
| 7,146,218 B2 | 12/2006 | Esteller et al. | |
| 7,176,817 B2 | 2/2007 | Jensen | |
| 7,215,269 B2 | 5/2007 | Lee et al. | |
| 7,221,303 B1 | 5/2007 | Melanson | |
| 7,230,555 B2 | 6/2007 | Dolazza et al. | |
| 7,233,198 B2 | 6/2007 | Niederkorn | |
| 7,245,246 B2 | 7/2007 | Ihs et al. | |
| 7,304,592 B2 | 12/2007 | Pinna et al. | |
| 7,345,607 B1 | 3/2008 | Frigaard et al. | |
| 7,355,539 B2 | 4/2008 | Petersen et al. | |
| 7,358,880 B1 | 4/2008 | Melanson | |
| 7,362,255 B1 | 4/2008 | Tsyrganovich | |
| 7,375,666 B2 | 5/2008 | Melanson | |
| 7,414,557 B2 | 8/2008 | Andersson et al. | |
| 2003/0146786 A1 | 8/2003 | Gulati et al. | |
| 2003/0184464 A1 | 10/2003 | Nakamura et al. | |
| 2004/0141558 A1 | 7/2004 | Plisch et al. | |
| 2005/0081847 A1 | 4/2005 | Lee et al. | |
| 2005/0128111 A1 | 6/2005 | Brooks | |
| 2005/0162222 A1 | 7/2005 | Hezar et al. | |
| 2006/0055456 A1 | 3/2006 | Niederkorn | |
| 2006/0135877 A1 | 6/2006 | Giftakis et al. | |
| 2006/0139192 A1 | 6/2006 | Morrow et al. | |
| 2006/0139193 A1 | 6/2006 | Morrow et al. | |
| 2006/0164272 A1 | 7/2006 | Philips et al. | |
| 2006/0173501 A1 | 8/2006 | Stickney et al. | |
| 2006/0250291 A1 | 11/2006 | Lyden et al. | |
| 2006/0293720 A1 | 12/2006 | DiLorenzo | |
| 2007/0032734 A1 * | 2/2007 | Najafi et al. | 600/513 |
| 2007/0077907 A1 | 4/2007 | Rector | |
| 2007/0152865 A1 | 7/2007 | Melanson | |
| 2007/0208262 A1 * | 9/2007 | Kovacs | 600/509 |
| 2007/0216562 A1 | 9/2007 | Teo et al. | |
| 2009/0079607 A1 | 3/2009 | Denison et al. | |

FOREIGN PATENT DOCUMENTS

| | | |
|---|---|---|
| EP | 1 777 825 A1 | 4/2007 |
| GB | 1 249 395 | 10/1971 |
| WO | WO 99/12264 | 3/1999 |
| WO | WO 02/01711 | 1/2002 |
| WO | WO 02/03087 | 1/2002 |
| WO | WO 2006/066098 | 6/2006 |

OTHER PUBLICATIONS

U.S. Appl. No. 11/861,856, filed Sep. 26, 2007 entitled "Capacitive Digital-to-Analog Converter Reset in an Implantable Medical Device Analog-to-Digital Converter".

Declaration Under 37 C.F.R. 1.132, 3 pgs., (signed by Michael W. Heinks on Jul. 7, 2009).

Reply to Written Opinion from corresponding PCT Application Serial No. PCT/US2008/009034 filed Jul. 8, 2009, 10 pgs.

Enz et al., "Circuit techniques for reducing the effects of op-amp imperfections: autozeroing, correlated double sampling, and chopperstabilization," Proceedings of the IEEE, vol. 84, No. 11, pp. 1584-1614, Nov. 1996.

Yen et al., "Micro-power low-offset instrumentation amplifier IC design for biomedical system applications," IEEE Transactions on Circuits and Systems, vol. 51, No. 4, pp. 691-699, Apr. 2004.

Harb et al., "New CMOS instrumentation amplifier dedicated to very low-amplitudesignal applications," Proceedings of ICECS, vol. 1, pp. 517-520, Sep. 1999.

Gosselin et al., "An ultra low-power chopper stabilized front-end for multichannel corrtical signals recording," Electrical and Computer Engineering, vol. 4, pp. 2259-2262, May 2004.

Harrison et al., "Local Field Potential Measurement with Low-Power Analog Integrated Circuit," Engineering in Medicine and Biology Society, 2004, IEMBS '04, 26$^{th}$ Annual International Conference of the IEEE, vol.: 2, On pp. 4067- 4070 vol. 6, Sep. 1-5, 2004.

Martins et al., "A CMOS IC for Portable EEG Acquisition Systems," IEEE Transactions on Instrumentation and Measurement, vol. 47, No. 5, pp. 1191-1196, Oct. 1998.

Boser, "Capacitive Interfaces for Monolithic Integrated Sensors," Chapter in "RF Analog-to-Digital Converters; Sensor and Actuator Interfaces; Low-Noise Oscillators, PLLs and Synthesizers," R.J. van de Plaasche, J.H. Huijsing, and W.M.C. Sansen (eds.), Kluwer Academic Publishers, Nov. 1997.

Bakker et al., "A CMOS Nested-Chopper Instrumentation Amplifier with 100-nV Offset," IEEE Journal of Solid-State Circuits, vol. 35, No. 12, pp. 1877-1883, Dec. 2000.

Sanduleanu et al., "A Low Noise, Low Residual Offset, Chopped Amplifier for Mixed Level Applications," IEEE, 0-7803-5008-1/98, pp. 333-336, Sep. 1998.

Hadiashar et al., "A Chopper Stabilized CMOS Analog Multiplier with Ultra Low DC Offsets," Solid-State Circuits Conference, pp. 364-367. Sep. 2006.

Yiqian Ying, "Chopper Stabilized Amplifiers," Term Paper, Department of Electrical and Computer Engineering, University of Toronto, 17 pgs., Nov. 12, 2001.

Yazicioglu et al., "A 60uV 60nV/rtHz Readout Front-End for Portable Biopotential Acquisition Systems," ISSCC Digest of Technical Papers 2006, paper 2.6, Feb. 2006.

Makinwa, "Dynamic Offset Cancellation Techniques," Smart Sensor Systems '02, May 2002.

Ng et al., "A CMOS Analog Front-End IC for Portable EEG/ECG Monitoring Applications," IEEE Trans. On Circuits and Systems, vol. 52 No. 11, Nov. 2005.

Burt et al., "A Micropower Chopper-Stabilized Operational Amplifier using an SC Notch Filter with Synchronous Integration inside the Continuous-Time Signal Path," ISSCC Digest of Technical Papers 2006, paper 19.6, Feb. 2006.

Harrison et al., "A Low-Power Low-Noise CMOS Amplifier for Neural Recording Applications," IEEE J. of Solid-State Circuits, vol. 38, No. 6 pp. 958-965, Jun. 2003.

Wu et al., "A IV 2.3mW Biomedical Signal Acquisition IC," ISSCC Digest of Technical Papers 2006, paper 2.7, Feb. 2006.

Harrison et al., "A Low-Power Integrated Circuit for a Wireless 100-Electrode Neural Recording System," ISSCC Digest of Technical Papers 2006, paper 30.2, Feb. 2006.

Peter G. Blanken et al., "A 10 μV-Offset 8kHz Bandwidth $4^{th}$-Order Chopped Sigma-Delta A/D Converter for Battery Management," Solid-State Circuits Conference, 2002, Digest of Technical Papers, 2002 IEEE International Feb. 3-7, 2002, vol. 1, Feb. 3, 2002, pp. 388-476 (XP-010585620).

International Search Report and Written Opinion from corresponding PCT Application Serial No. PCT/US2008/009034 mailed Nov. 20, 2008 (12 pages).

\* cited by examiner

IMPLANTABLE MEDICAL DEVICE WITH LOW POWER DELTA-SIGMA ANALOG-TO-DIGITAL CONVERTER

TECHNICAL FIELD

This disclosure relates to implantable medical devices and, more particularly, reducing power consumption in implantable medical devices.

BACKGROUND

In a variety of applications, implantable medical devices are used for one or both of monitoring or delivering therapy to a patient. For example, cardiac pacemakers typically monitor electrical signals from the heart, i.e., an electrocardiogram (ECG), and deliver electrical stimulation to the heart, via electrodes. The electrodes may be positioned within the heart, and coupled to the pacemaker by intravenous leads, or may be positioned subcutaneously using any non-intravenous location, such as below the muscle layer or within the thoracic cavity, for example.

In the case of demand pacing, for example, a cardiac pacemaker monitors the ECG to determine whether an intrinsic cardiac depolarization, e.g., a P-wave or R-wave, occurs within a rate interval. If an intrinsic depolarization occurs, the pacemaker resets a timer and continues to monitor the electrical signals from the heart. If an intrinsic depolarization does not occur, the pacemaker delivers one or more electrical pulses to the heart, and resets the timer.

Many pacemakers have used analog circuitry to process the ECG, e.g., to detect P-waves and R-waves. Implementation of digital signal processing for this purpose would be desirable, but would require relatively high resolution analog-to-digital conversion of the ECG. Increased resolution for analog-to-digital conversion generally requires higher oversampling of the analog signal, or more complex comparator circuitry, both of which increase the amount of current drain associated with the analog-to-digital conversion. Increased current drain is a concern in implantable medical devices, and particular in primary cell devices, where it may shorten the life of the power source of the implantable medical device, thereby requiring earlier explanation and replacement of the implantable medical device. Minimization of power consumption is also desirable for implantable medical devices with rechargeable power sources to, for example, reduce the frequency of recharging events and thereby increase the convenience of the implantable medical device from the perspective of the patient.

Another example application for digital signal processing in implantable medical device is analysis of electrical signals within the brain, e.g., an electroencephalogram (EEG), sensed via electrodes. An implantable medical device may analyze an EEG to, for example, identify epileptic seizures, or other neurological issues. In some cases an implantable medical device may deliver electrical stimulation to the brain, or other tissue within the patient, in response to or based on the analysis of the EEG. Furthermore, digital signal processing may be used in implantable medical devices to analyze any of a variety of signals generated by any of a variety of sensors based on physiological parameters of a patient, such as pressure, impedance, temperature, or physical motion.

SUMMARY

In general, this disclosure describes techniques for reducing power consumption within an implantable medical device (IMD). An IMD implanted within a patient may have finite power resources that are intended to last several years. To promote device longevity, sensing and therapy circuits of the IMD are designed to consume small levels of power. To this end, a sensing circuit of IMD may incorporate a delta-sigma analog-to-digital converter (ADC) designed in accordance with the techniques disclosed herein, which provides relatively high resolution output at a relatively low operation frequency, and does so with relatively low power consumption. An ADC designed in accordance with the techniques described herein utilizes a quantizer that has a lower resolution than a digital-to-analog converter (DAC) used for negative feedback. In one embodiment, the resolution of the DAC may include at least four times as many bits as the resolution of the quantizer. For example, the ADC may utilize a single bit comparator that drives an up-down counter, which then drives an 8-bit DAC feedback. This configuration provides the benefits of higher resolution DAC feedback, i.e., increased precision to allow for lower quantization noise, without having the use high oversampling ratios that result in high power consumption.

In one embodiment, an implantable medical device comprises at least one sensor that generates an analog input signal, at least one delta-sigma analog-to-digital converter (ADC) that converts the analog input signal to a digital signal and a processor that receives the digital signal from the delta-sigma ADC. The delta-sigma ADC includes a quantizer that produces a control signal based on an integrated difference between the analog input signal and a reconstruction of the analog input signal, an up/down counter that adjusts a digital value according to the control signal, and a digital-to-analog converter (DAC) that generates the reconstruction of the analog input signal based on the digital value of the up/down counter and provides the reconstruction of the analog input signal as negative feedback to the integrator. A resolution of the quantizer is less than a resolution of the DAC.

In another embodiment, a method comprises receiving an analog input signal from at least one sensor of an implantable medical device, converting the analog input signal to a digital signal using at least one delta-sigma analog-to-digital converter (ADC), and sending the digital signal from the delta-sigma ADC to a processor for analysis. Converting the analog input signal to the digital signal comprises producing, with a quantizer, a control signal based on an integrated difference between the analog input signal and a reconstruction of the analog input signal, adjusting a digital value of an up/down counter according to the control signal, and generating the reconstruction of the analog input signal based the digital value of the up/down counter using a digital-to-analog converter (DAC). The resolution of the quantizer is less than the resolution of the DAC.

In another embodiment, an implantable medical device comprises means for generating an analog input signal, means for converting the analog input signal to a digital signal, and means for analyzing the digital signal from the converting means. The converting means includes means for producing a control signal at a first resolution based on an integrated difference between the analog input signal and a reconstruction of the analog input signal, means for adjusting a digital value according to the control signal, and means for generating the reconstruction of the analog input signal at a second resolution based on the digital value. The first resolution is less than the second resolution.

The details of one or more embodiments are set forth in the accompanying drawings and the description below. Other features, objects, and advantages of these embodiments will be apparent from the description and drawings, and from the claims.

DETAILED DESCRIPTION

Figure 1:
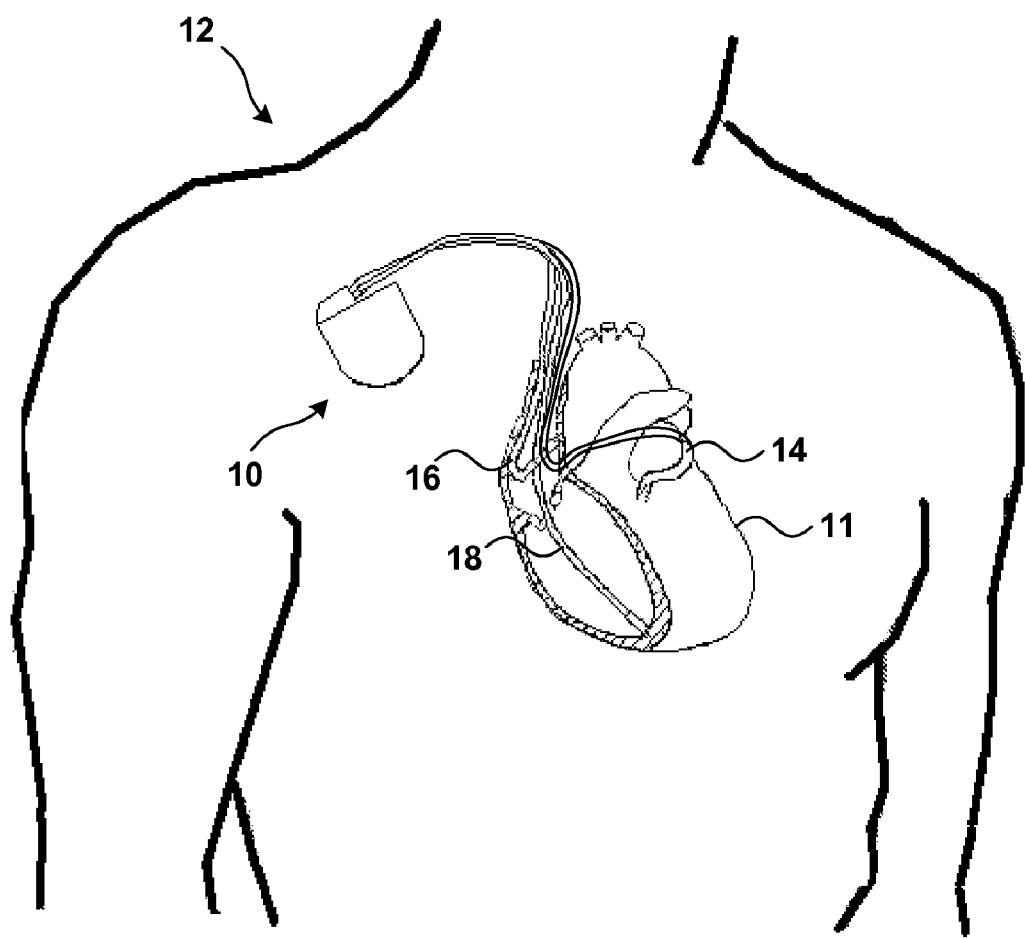
FIG. 1 is a conceptual diagram illustrating an example implantable medical device (IMD) implanted within a patient.

FIG. 1 is a conceptual diagram illustrating an implantable medical device ("IMD") 10 implanted within a patient 12. IMD 10 is implanted near a heart 11 of patient 12. Patient 12 ordinarily will be a human patient. In some cases, however, IMD 10 may be used within non-human patients. IMD 10 includes leads 14, 16 and 18 that extend from IMD 10 to heart 11 of patient 12. In the example illustrated in FIG. 1, leads 16 and 18 extend from IMD 10 to the right atrium and ventricle, respectively, of heart 11. Lead 14 extends from IMD 10 into the coronary sinus of heart 11, proximate to the left ventricle of the heart. Although the example IMD 10 illustrated FIG. 1 includes three leads, IMD 10 may be coupled to any number of leads that are located within or near heart 11.

Leads 14, 16 and 18 include one or more electrodes that may be used for sensing one or more parameters of heart 11 and/or delivering therapy to heart 11. The electrodes may, for example, sense one or more electrical signals attendant to the depolarization and repolarization of the heart 11, e.g., an electrocardiogram (ECG), and leads 14, 16 and 18 may convey the sensed signals to IMD 10. IMD 10 may also deliver therapy, e.g., in the form of one or more pulses, to heart 11 via leads 14, 16 and/or 18.

In the illustrated example, IMD 10 is an implantable pacemaker-cardioverter-defibrillator (PCD) that provides pacing pulses for causing depolarization of cardiac tissue via one or more electrodes on leads 14, 16 and/or 18. IMD 10 may operate in a demand pacing mode, in which IMD 10 delivers pacing pulses based on the absence of an intrinsic depolarization in the ECG. As a PCD, IMD 10 also provides cardioversion or defibrillation pulses, or high-rate tachyarrhythmia pacing pulses, for treating cardiac arrhythmias, atrial fibrillation, ventricular fibrillation or tachyarrhythmia via one or more electrodes on leads 14, 16 and/or 18. In such embodiments, IMD 10 analyzes the ECG to identify the cardiac arrhythmias, e.g., based on heart rate and/or ECG morphology. In other embodiments, IMD 10 may be an implantable pacemaker that does not provide cardioversion or defibrillation pulses, or high-rate tachyarrhythmia pacing pulses, for treating cardiac arrhythmias, atrial fibrillation, ventricular fibrillation or tachyarrhythmia, or an implantable cardioverter-defibrillator (ICD) that does not provide pacing pulses for causing depolarization of cardiac tissue.

Because IMD 10 is implanted within patient 12, IMD 10 may have finite power resources that are intended to last several years. To promote device longevity, sensing and therapy circuits of IMD 10 are designed to consume small levels of power. To this end, a sensing circuit of IMD 10 incorporates an analog-to-digital converter (ADC) designed in accordance with the techniques disclosed herein, which provides relatively high resolution output at a relatively low operation frequency, and does so with relatively low power consumption.

The IMD 10 illustrated in FIG. 1 is an example of the type of device in which various techniques described in this disclosure may be embodied, and is not to be considered as limiting of the scope of the claimed invention. The techniques described herein may be practiced in a wide variety of medical device implementations. Additional example applications of the various techniques described herein with reference to cardiac pacemaker IMD 10 are discussed below.

Figure 2:
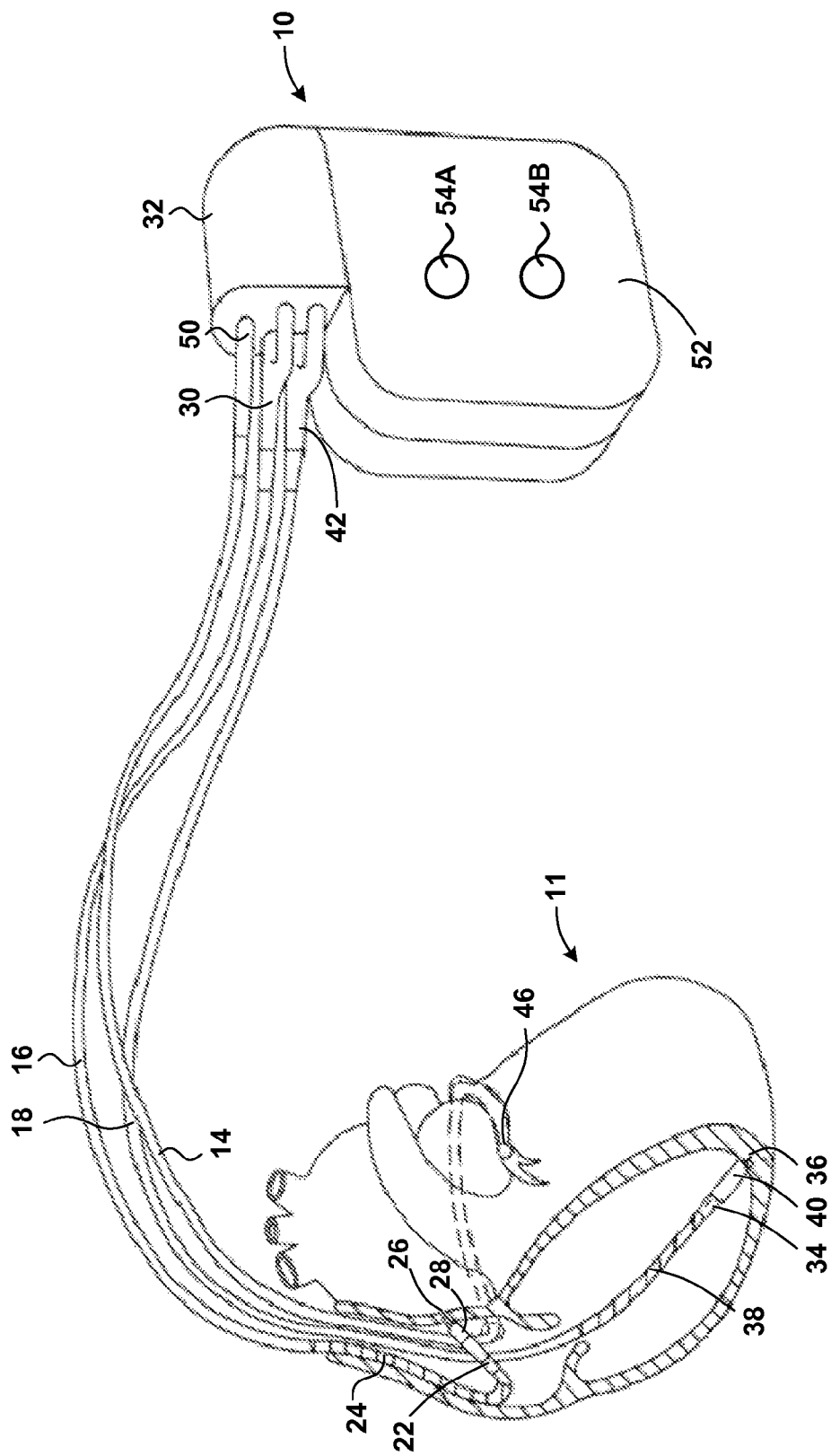
FIG. 2 is a conceptual diagram illustrating the IMD of FIG. 1 in conjunction with a human or mammalian heart in further detail.

FIG. 2 is a conceptual diagram illustrating IMD 10 in conjunction with human or mammalian heart 11, and in further detail. The specific structure of IMD 10 is described below for purposes of example, and should not be considered limiting of the invention.

As shown in FIG. 2, IMD 10 may include an atrial lead 16, which may include an elongated insulative lead body carrying three concentric coiled conductors, separated from one another by tubular insulative sheaths. Located adjacent the J-shaped distal end of atrial lead 16 is a ring electrode 22, an elongated coiled electrode 24, and an extendable helix electrode 26 mounted retractably within an insulative electrode head 28. Each of electrodes 22, 24 and 26 is coupled to one of the coiled conductors within the body of lead 16. Electrodes 22, 24 and 26 are employed for atrial pacing and for sensing atrial depolarizations, often referred to as atrial events or P-waves. At the proximal end of atrial lead 16 is a bifurcated connector 30 that is inserted into a connector block 32 associated with IMD 10. In particular, bifurcated connector 30 carries three electrical connectors, each coupled to one of the coiled conductors.

IMD 10 may also include a ventricular lead 18 having an elongated insulative lead body carrying three concentric coiled conductors, separated from one another by tubular insulative sheaths. Located adjacent the distal end of ventricular lead 18 are a ring electrode 34, an extendable helix electrode 36 mounted retractably within an insulative electrode head 40 and an elongated coil electrode 38. Each of electrodes 34, 36 and 38 is coupled to one of the coiled conductors within the lead body of ventricular lead 18. Electrodes 34, 36 and 38 can be used for both cardiac pacing and sensing of ventricular depolarizations, often referred to as ventricular events or R-waves. At the proximal end of ventricular lead 18 is a bifurcated connector 42 that is inserted into a connector block 32, and carries three electrical connectors, each coupled to one of the coiled conductors.

A coronary sinus lead 14 includes an elongated insulative lead body carrying one coiled conductor coupled to an elongated coiled defibrillation electrode 46. Electrode 46, illustrated in broken outline, is located within the coronary sinus and great vein of the heart. In some embodiments, however, lead 14 may be located within the left ventricle and configured similarly to lead 18, i.e., as a ventricular lead with ring and tip electrodes for delivery of pacing pulses. At the proximal end of lead 14 is a connector plug 50 that is inserted into carrier block 32, and carries an electrical connector, coupled to the coiled conductor.

In the illustrated embodiment, IMD 10 also includes electrodes 54A and 54B (collectively "electrodes 54") on or within the housing 52 of IMD 10. IMD 10 may include any number of electrodes 54, which may, for example, be used for capture detection or far-field ECG detection. Electrodes 54 may also function as a subcutaneous defibrillation and/or cardioversion electrodes for defibrillation and/or cardioversion of either the atria or ventricles.

Figure 3:
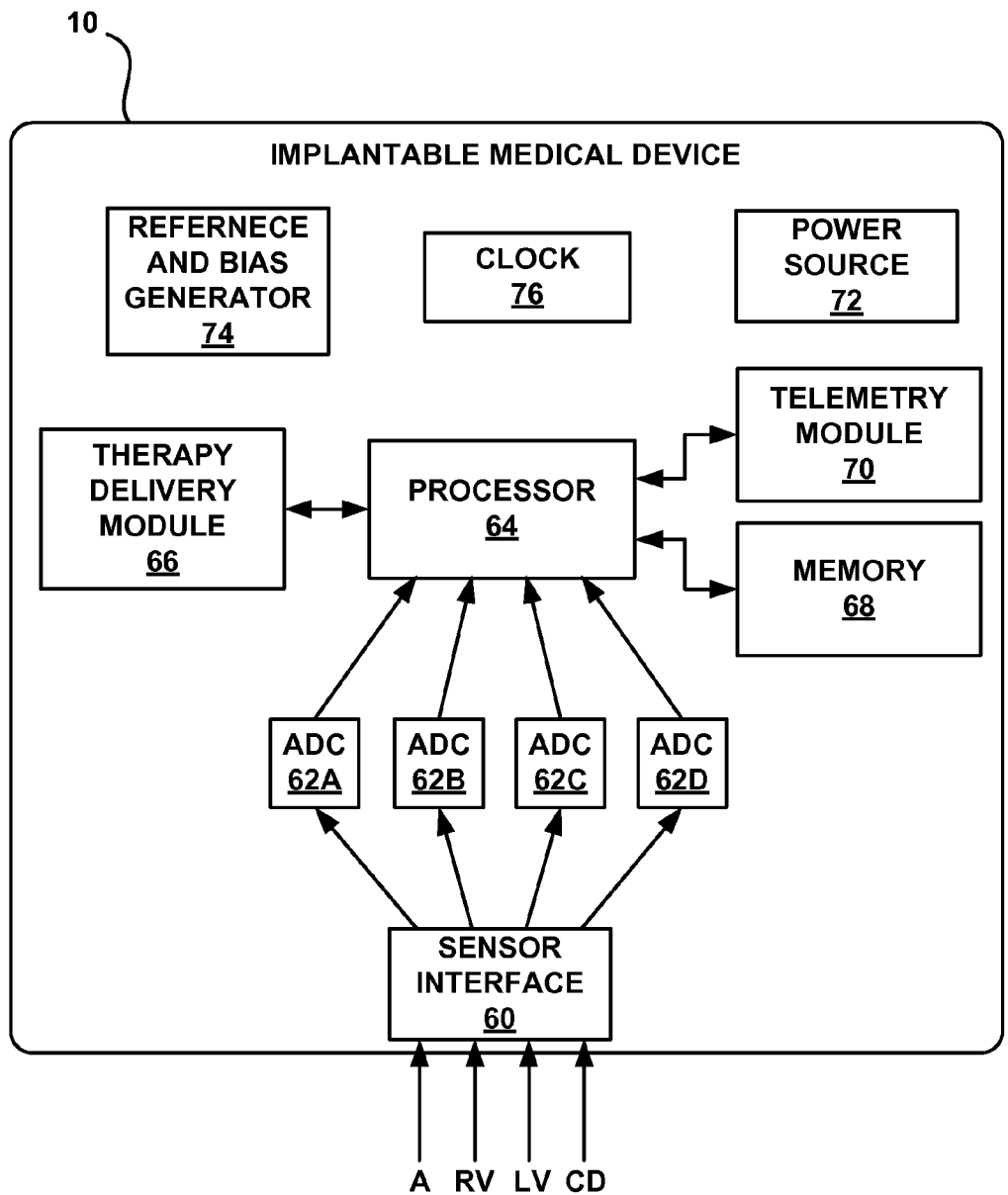
FIG. 3 is a block diagram of the IMD of FIG. 1.

FIG. 3 is a functional block diagram further illustrating IMD 10. In the example illustrated in FIG. 3, IMD 10 includes a sensor interface 60, ADCs 62A-62D (collectively, "ADCs 62"), a processor 64, a therapy delivery module 66, a memory 68, a telemetry module 70, a power source 72, a reference and bias generator 74 and a clock 76. In the example illustrated in FIG. 3, IMD 10 is a cardiac pacemaker-cardioverter-defibrillator that provides pacing pulses for causing depolarization of cardiac tissue, as well as cardioversion and/or defibrillation pulses, or high-rate pacing, for terminating arrhythmias. Alternatively, IMD 10 may provide other therapies, or be dedicated to sensing, i.e., patient monitoring. In either case, IMD 10 makes use of sensed signals received from one or more sensors via sensor interface 60.

IMD 10 receives signals from one or more sensors and controls delivery of the pacing pulses based on the received signals. Sensor interface 60 of IMD 10 couples to the one or more sensors for receiving the sensed signals. For example, sensor interface 60 may couple to electrodes of one or more leads, such as electrodes 22, 24, 26, 34, 36, 38 and/or 46 of leads 14, 16 and 18 (FIG. 2). In this manner, sensor interface 60 may couple IMD 10 to one or more sensors located outside of IMD 10. Sensors located outside of IMD 10 may be coupled to IMD 10 via leads, or wirelessly coupled to IMD 10. Additionally or alternatively, sensor interface 60 may couple to sensors located on or within a housing of IMD 10. For example, sensor interface 60 may couple to electrodes 54 located on or within the housing of IMD 10 (FIG. 2).

In the example illustrated in FIG. 3, sensor interface receives sensed signals on four channels from electrodes 22, 24, 26, 34, 36, 38 and/or 46 of leads 14, 16 and 18 and electrodes 54 on or within housing 52. In particular, sensor interface 60 receives sensed signals from one or more electrode located in the atrium of a heart of a patient (labeled 'A'), one or more electrodes located in the right ventricle of the heart (labeled 'RV'), one or more electrodes located within the left ventricle of the heart (labeled 'LV'), and one or more electrodes that provide capture detection (labeled 'CD'). The electrodes that provide capture detection may be a different electrode vector of one or more of the electrodes of leads 14, 16, and 18. Although IMD 10 is described as receiving sensed cardiac signals, sensor interface 60 may couple to any type of sensor or combination of sensors. For example, sensor interface 60 may be coupled to a pressure sensor, an accelerometer, an activity sensor, an impedance sensor, a temperature sensor, an acidity sensor, or the like. In addition to physiological parameters, sensor interface 60 may couple sensors that monitor parameters other than physiological parameters, e.g., ambient conditions such as pressure or temperature.

Sensor interface 60 provides each of the received signals to a respective one of ADCs 62, which convert the received signal to a digital signal that represents the analog signal. Thus, multiple ADCs 62 are available to support multiple sensing channels. As described above, the multiple sensing channels illustrated in FIG. 3 measure physiological information of different locations in the heart. Although in the example illustrated in FIG. 3, each sensing channel corresponds to its own ADC 62, IMD 10 may have more or fewer ADCs. For example, IMD 10 may include two ADCs and multiplex the input signals into the ADCs such that two input channels are converted from analog to digital using a common ADC. Other combinations or configurations of ADCs may be used.

ADCs 62 provide the digital signal that represents the analog signal to processor 64. Processor 64 may store the digital signals, portions thereof, or values determined based thereon, in memory 68. Processor 64 may include at least one microprocessor, microcontroller, digital signal processor (DSP), application specific integrated circuit (ASIC), field programmable gate array (FPGA), discrete logic circuitry, or a combination of such components. Memory 68 may include any combination of volatile, non-volatile, magnetic, optical, or solid state media, such as read-only memory (ROM), random access memory (RAM), electronically-erasable programmable ROM (EEPROM), flash memory, or the like.

Processor 64 may transmit the signal, or values determined based on the signal, to an external programmer, via wireless telemetry via telemetry module 70. Telemetry module 70 may include a receiver and a transmitter. Processor 64 may control telemetry module 70 to communicate with the external programmer on a continuous basis, at periodic intervals, or upon request from the external programmer. In addition, in some embodiments, telemetry module 70 may support wireless communication with one or more wireless sensors that sense physiological signals and transmit the signals to IMD 10. The information transmitted via telemetry module 70 may be used by a physician to monitor the condition of the patient, or the efficacy of therapy if IMD 10 delivers therapy. Telemetry module 70 may comprise known circuitry for wireless communication according to any of a variety proprietary or non-proprietary local wireless communication standards.

Processor 64 may also control delivery of therapy to the patient by therapy delivery module 66 based on signals received via sensor interface 60. In the illustrated cardiac pacemaker embodiment, therapy delivery module 66 includes pulse generation circuitry, which may include one or more capacitors, regulators, switches and the like for delivery of pulses or substantially continuous signals, such as sinusoidal signals, to selected chambers of heart 11 via selected ones of electrodes 22, 24, 26, 34, 36, 38 and/or 46 of leads 14, 16 and 18 or electrodes 54 on or within housing 52.

For example, processor 64 may control therapy delivery module 66 to deliver one or more pacing pulses based on the absence of an intrinsic pulse in an ECG detected via one of the sensing channels A, RV, or LV. Such demand pacing is one example in which processor 64 controls therapy delivery module 66 to deliver therapy in response to a sensed signal, i.e., provides responsive therapy. As another example, processor 64 may control therapy delivery module 66 to provide one of the above-discussed arrhythmia termination therapies, based on the sensed signals. Processor 64 may, for example, analyze the digital signals to determine whether the patient is experiencing an arrhythmia and control therapy delivery module 66 to deliver one or more defibrillation or cardioversion pulses when an arrhythmia is detected.

Therapy delivery module 66 may be configured to provide unipolar stimulation or bipolar stimulation. Thus, therapy delivery module 66 may deliver pulses via two or more electrodes on one lead (i.e., bipolar stimulation) or via one electrode on a lead and one of housing electrodes 54 of IMD 10 (i.e. unipolar stimulation). Processor 64 may additionally control therapy delivery module 66 to deliver electrical stimulation with different pulse amplitudes, pulse widths, frequencies (i.e., pulse rates), electrode configurations, or the like based on the sensed signals.

Although IMD 10 FIG. 3 is described in the context of delivering electrical pulses to treat cardiac disorders, IMDs according to various embodiments of the invention may generate and deliver stimulation energy for treatment of any of a variety disorders, such as deep brain stimulation (DBS) for movement disorders, psychological discords, epilepsy or pain; spinal cord stimulation (SCS) for pain; pelvic stimulation for pelvic pain, incontinence, or sexual dysfunction; gastric stimulation for gastroparesis, obesity or other disorders; or peripheral nerve stimulation for pain. Another example is muscle stimulation, e.g., functional electrical stimulation (FES) to promote muscle movement or prevent atrophy. The description of IMD 10 as providing cardiac stimulation is provided only as an example, and should not be considered limiting of the types of IMDs in which the techniques described herein may be utilized.

Alternatively, or in addition to providing electrical stimulation, IMD 10 may be configured to provide therapy by delivering fluid to the target site through one or more fluid delivery devices. In embodiments in which one or more fluid delivery devices are part of the therapy elements associated with therapy delivery module 66, therapy delivery module 66 may include one or more fluid reservoirs and one or more pump units that pump fluid from the fluid reservoirs to the target site through the fluid delivery devices. The fluid reservoirs may contain a drug or mixture of drugs. The fluid reservoirs may provide access for filling, e.g., by percutaneous injection of fluid via a self-sealing injection port. The fluid delivery devices may comprise, for example, catheters that deliver, i.e., infuse or disperse, drugs from the fluid reservoirs to the same or different target sites. In this case, processor 64 and therapy delivery module 66 may control which drugs are delivered and the dosage of the drugs delivered based on the sensed signals.

Therapy delivery module 66, processor 64, telemetry module 70, memory 68, sensor interface 60 and ADCs 62 may receive operating power from power source 72. Power source 72 may take the form of a small, rechargeable or non-rechargeable battery, or an inductive power interface that transcutaneously receives inductively coupled energy. In the case of a rechargeable battery, power source 72 similarly may include an inductive power interface for transcutaneous transfer of recharge power.

Minimization of power consumption is desirable for embodiments in which power source 72 is non-rechargeable to prolong the useful life of IMD 10. Minimization of power consumption is also desirable for embodiments in which power source 72 is rechargeable to, for example, reduce the frequency of recharging events and thereby increase the convenience of IMD 10 from the perspective of the patient. To this end, each of ADCs 62 is a delta-sigma ADC that is configured to provide accurate output for low frequency signals, e.g., signals that are smaller than 100 Hz, with low power consumption, or for signals that have frequencies that are significantly smaller than the clocking frequency (e.g., 1 kHz signals while clocking at 16 kHz). Note that for other IMD applications, such as with drug pumps, the practical clocking frequencies may extend upward to several hundred kilohertz, e.g. 1 kHz signal bandwidth with 50 KHz clocking. To do so, ADCs 62 utilize a quantizer that has a lower resolution than a digital-to-analog converter (DAC) used for negative feedback. DAC may comprise at least a 6-bit DAC. In one embodiment, for example, ADCs 62 may utilize a single bit comparator that drives an up-down counter, which then drives an 8-bit DAC feedback. This configuration provides the benefits of higher resolution DAC feedback, i.e., increased precision to allow for lower quantization noise, without having the use high oversampling ratios that result in high power consumption.

Reference and bias generator 74 supplies reference voltages and/or currents to ADCs 62 and any other circuitry of IMD 10 that requires reference voltages and/or currents. Furthermore, reference and bias generator 74 supplies any bias voltages and/or currents to ADCs 62 and any other circuitry of IMD 10 that requires bias voltages and/or currents. Likewise, clock 76 supplies a clock signal to ADCs 62 and any other circuitry of IMD 10 that needs to be clocked.

Figure 4:
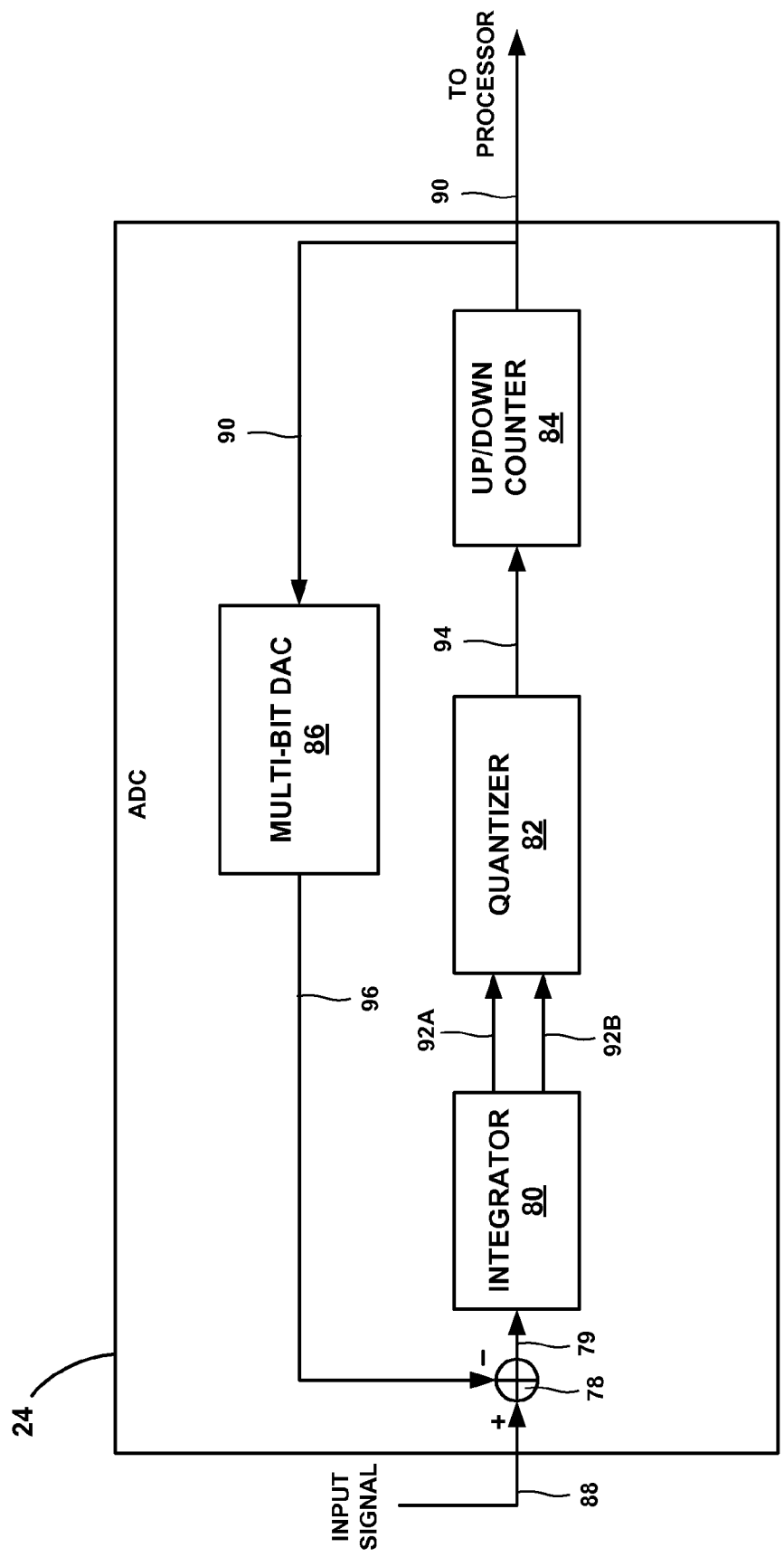
FIG. 4 is a block diagram illustrating an example delta-sigma analog-to-digital converter (ADC) that is configured to provide stable output at for input signals with low frequency while consuming relatively low power.

FIG. 4 is a block diagram illustrating an example delta-sigma ADC 62 that is configured to provide stable output at for input signals with low frequency with relatively low power compared to ADCs that use higher oversampling rates or higher order comparators. As shown in FIG. 4, ADC 62 includes a difference circuit 78, an integrator 80, a quantizer 82, an up/down counter 84 and a multi-bit DAC 86 that provides a feedback path. ADC 62 operates as a continuous time system. In the illustrated embodiment, ADC 62 utilizes a differential architecture that includes a differential integrator that outputs differential signals that are substantially the same in magnitude and substantially opposite in polarity (e.g., 180 degrees out of phase). Other architectures may, however, be used without departing from the scope of this disclosure. In general, ADC 62 is configured to convert a low frequency analog input signal 88 into a digital signal 90. Example low frequency signals include physiological signals and other signals having a frequency of less than approximately 100 Hz. ADC 62 may also be used to accurately convert analog input signals with frequencies that are significantly smaller than a clock frequency used to drive ADC 62. As described above, analog input signal 88 may be obtained from any of a variety of sensors, such as electrodes of one or more leads.

DAC 86 converts digital signal 90 into a reconstructed representation 96 of analog input signal 90, and thereby provides a feedback path for ADC 62. In particular, reconstructed representation 96 is applied to difference circuit 78 as a negative feedback. Difference circuit 78 generates a difference signal 79 representative of the difference between input signal 88 and reconstructed signal 96 and provides the difference signal to an input of integrator 80. Integrator 80 integrates the difference signal 79 provided by difference circuit 78. In other words, integrator 80 integrates the output according to the difference between input signal 90 and reconstructed representation 96. The integration slope is defined by the voltage to current gain of integrator 80 and an integration capacitor value at integrator 80 outputs.

In the example illustrated in FIG. 4, integrator 80 is a differential integrator. As will be described in more detail in FIG. 5, integrator 80 may include a transconductance amplifier that outputs differential current signals that represent the difference between input signal 90 and reconstructed representation 96. The differential current signals drive capacitive loads that effectively integrate the difference signal 79 to generate differential voltage signals 92A and 92B. Common mode feedback local to the integrator 80 maintains a constant common mode voltage at the outputs 92A and 92B. The differential voltage signal 92A and 92B are of an equal magnitude and opposite polarities, and represent the integrated difference between input signal 88 and reconstructed signal 96. However, integrator 80 need not be a differential integrator.

Differential integrators provide the advantage of being less affected by any common mode shift in the output voltage. Disturbances at the differential outputs are both shifted by approximately the same amount, thus resulting in little or no change in the difference between the differential outputs. Common mode shifts in the differential output voltages 92A and 92B are rejected by quantizer 82. In other words, noise or other disturbances will affect each of differential signals 92A and 92B equally. Thus, the difference between the two signals is relatively unaffected. Typically, the output difference voltage is small because analog input signal 88 does not experience large signal changes. Consequently, ADC 62 can track changes in analog input signal 88 to produce digital to analog signal 96 as an accurate approximation of input signal 88.

Quantizer 82 produces a quantization signal 94 that represents a level of the integrated difference between the input signal 88 and the reconstructed signal 96. In the case of a 1-bit quantizer, e.g., a single bit comparator, the output of the comparator is a signal that represents a binary +1 or −1 (or, in some cases either a binary '1' or '0') based on a comparison of the differential signals output by integrator 82. If differential signal 92A is greater than differential signal 92B, which indicates the accumulated error signal is positive signaling that, on average, the integrated input signal 88 is larger than the integrated reconstructed signal 96, the comparator outputs a value of +1. If differential signal 92A is less than differential signal 92B, which indicates the accumulated error signal is negative signaling that, on average, the integrated input signal 88 is smaller than the integrated reconstructed signal 96, the comparator outputs a value of −1, or 0.

In this manner, the 1-bit quantizer determines the sign of the integrated difference, i.e., whether the integrated difference is positive or negative. In other embodiments, quantizer 82 may be a multi-bit quantizer. For example, quantizer 82 may comprise a 2-bit quantizer. In this case, the output of the 2-bit quantizer may represent a +1, 0, or −1 based on the comparison of the differential signals output by integrator 80. In the case of multi-bit quantizers, the quantizer determines not only the sign of the output difference, i.e., whether the output difference is positive or negative, but also the magnitude of the output difference. The higher the resolution of quantizer 82, the more complex quantizer 82 becomes and the more power that is consumed by quantizer 82. If ADC 62 does not operate using a differential architecture, quantizer 82 may produce a quantization signal that represents the level of difference between the output of integrator 80 and a reference voltage.

Quanitzed signal 94 controls up/down counter 84. In the case of a 1-bit quantizer, quantized signal 94 may be equal to either +1 or −1 (or 0). When quantized signal 94 is equal to +1, quantized signal 94 causes up/down counter 84 to count up. However, when quantized signal is equal to −1 (or 0), quantized signal causes up/down counter 84 to count down. In the case of a multi-bit quantizer, up/down counter 84 may count up and down by larger values or remain at the current count in the case of the quantized signal equaling zero. In this manner, ADC 62 generates digital signal 96 as a digital bit stream that approximates analog input signal 88. The combination of integrator 80 and up/down counter 84 operates as a double integrator that provides decreased stability. Loop compensation may help to maintain stability of the converter. This compensation can be implemented using analog or digital techniques as described in detail below.

DAC 86 is multi-bit DAC that uses digital signal 90 to generate the reconstructed representation of input signal 88, i.e., reconstructed signal 96. As described above, DAC 86 forms a feedback path that applies reconstructed signal 96 as negative feedback to the input of integrator 80. DAC 86 provides continuous feedback in a stable manner to integrate the error between input signal 88 and reconstructed signal 96. As described herein, the resolution of DAC is higher than the resolution of quantizer 82. In one embodiment, for example, quantizer 44 may comprise a single bit comparator that drives an up-down counter, which then drives an 8-bit feedback DAC.

This configuration provides the benefits of higher resolution DAC feedback.

The result is increased precision due to lower quantization noise without using high oversampling ratios or higher order loop filtering that consume large amounts of energy. The increased precision may thereby reduce oversensing that could result in providing therapy when it is not needed. For example, the increased precision may reduce oversensing of intrinsic depolarizations in an ECG signal, which could lead to improper delivery of pacing pulses. Additional advantages are discussed in this disclosure or may occur to those skilled in the art upon consideration of this disclosure. Moreover, such advantages may not coexist in every embodiment.

The feedback loop of ADC 62 may have an operating frequency that is higher than the frequency at which the digital signal 90 is output to the processor. In other words, ADC 62 may integrate the error between input signal 88 and reconstructed signal 96 using oversampling. In one embodiment, the feedback loop of ADC 62 may have an operating frequency of 16 kHz or 32 kHz while the frequency at which digital signal 90 is output to the processor may be 1 kHz. In other words, the feedback loop of ADC 62 integrates the error between input signal 88 and reconstructed signal 96 at approximately 16 or 32 times the rate at which the digital signal is output. Nonetheless, the high resolution feedback provided by the multi-bit DAC may further provide the advantage of a lower oversampling ratio, i.e., lower operating frequency of the feedback loop, relative to embodiments with a lower resolution DAC.

ADC 62 may be useful in many different applications. This disclosure presents various example embodiments of ADC 62. However, these example embodiments should not be considered limiting of the ADC 62 as broadly embodied and described in this disclosure. Rather, it should be understood that the example embodiments described in this disclosure are a subset of many different example embodiments within the scope of this disclosure.

Figure 5:
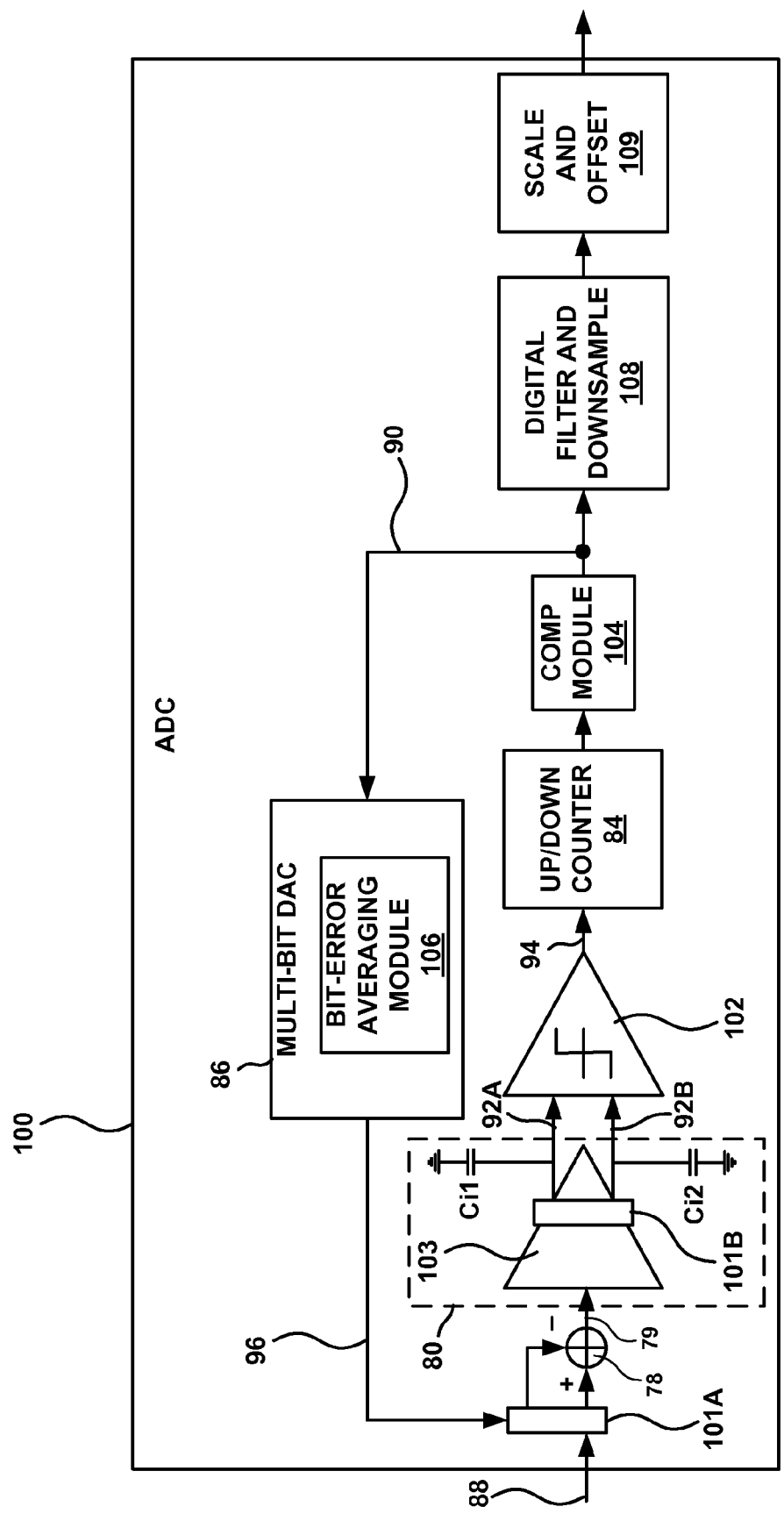
FIG. 5 is a diagram illustrating another example delta-sigma ADC.

FIG. 5 is a diagram illustrating an example delta-sigma ADC 100 in more detail. ADC 100 may represent, for example, ADC 62 of FIG. 4. ADC 100 receives an input signal 88 from a sensor. A chopper module 101A chops input signal 88 and reconstructed signal 96 up to the carrier (chop) frequency prior to application of the input signal to difference circuit 78. The original baseband signal components of input signal 88 and reconstructed signal 96 may have a frequency within a range of 0 to approximately 100 Hz and the carrier frequency may be approximately 4 kHz to approximately 16 kHz. It should be understood, however, that ADC 100 may be used for input signals with other frequency ranges and chop frequencies. For example, ADC 100 may be used in other implementations in which the input signal has a frequency that is significantly less than the clock frequency (e.g., an input signal of 1 kHz and a clock frequency of 50 kHz). Chopping the inputs to the carrier frequency may allow segregation of the original low frequency components from low frequency noise, e.g., noise from one or more components of ADC 100 or external signals that may enter the signal pathway at a low (baseband) frequency.

The chopped signals are provided to difference circuit 78, which generates a difference signal 79 representative of the difference between input signal 88 and reconstructed signal 96. Difference circuit 78 provides the difference signal to an input of integrator 80. In particular, integrator 80 includes a transconductance amplifier 103, a second chopper module 101B and a pair of capacitors Ci1 and Ci2. Difference signal 79 is amplified by transconductance amplifier 103. Chopper module 101B may modulate the amplified difference signal to upmodulate noise from the amplifier to the carrier frequency and demodulate the original baseband signal components from the carrier frequency back to baseband. In other words, chopper module 101B segregates the noise and the signal of interest. The clock signals driving chopper modules 101A and 101B should be synchronous with each other. In some embodiments, the clock signals driving chopper modules 101A and 101B may be the same signal, i.e., supplied by the same clock. In the example illustrated in FIG. 5, chopper module 101B is located within transconductance amplifier 103, but may be a separate component, e.g., a separate modulator. As described above, the signal output by transconductance amplifier 103 and chopper module 101B is a differential current.

Capacitors Ci1 and Ci2 function as an integrator that converts the differential current into a differential voltage. Moreover, capacitors Ci1 and Ci2 operate on the demodulated signal to pass the low frequency input signal components at baseband and substantially eliminate noise components that are located at the carrier frequency. In this manner, integration may be designed to provide a stable feedback path with acceptable bandwidth while also filtering out the upmodulated random telegraph signal ("RTS" or popcorn) noise, 1/f noise, and offset from the measurement band. In other words, integrator 80 provides first order filtering of the upmodulated noise. One method of compensating the sigma delta feedback loop is to add a pole zero resistor capacitor network to integrator 80 outputs 92A and 92B. In other embodiments, compensation may be provided by other circuitry. However, the use of integrator 80 as described in this disclosure may be desirable to reduce power consumption. Integrator 80 outputs differential voltage signals 92A and 92B that represent the integrated voltage difference between input signal 88 and reconstructed feedback 96. Differential signals have an equal magnitude and opposite polarities. In one embodiment, integrator 80 may comprise a continuous time fully differential Gm/C integrator. The Gm/C integrator may be useful because it consumes relatively little power. Moreover, Gm/C integrators are generally limited by input differential range (i.e., the difference from DAC to input) of about 150 mV, thereby providing a linear circuit over a limited differential range. A high resolution DAC is helpful in that it helps limit the difference signal applied to the integrator. In other embodiments, however, integrator 80 may comprise a different type of differential integrator or a non-differential integrator.

The differential outputs 92A and 92B of integrator 80 are input to a comparator 102. Comparator 102 samples differential signals 92A and 92B to resolve the sign of the integrator output. The sign of the integrator output, i.e., whether 92A is greater than 92B or 92B is greater than 92A, indicates whether the accumulated (integrated) error signal is positive or negative.

In one embodiment, comparator 102 may be a differentially strobed comparator. For example, comparator 102 may be strobed at an operating frequency of 16 kHz or 32 kHz. Thus, comparator may sample differential signals 92A and 92B at a sampling frequency of 16 or 32 kHz. In this manner, comparator 102 functions as a single bit quantizer. In other embodiments, however, a multi-bit quantizer that has a lower resolution than multi-bit DAC 86 may be used.

Up/down counter 84 is driven by the output of comparator 102 such that up/down counter 84 is incremented and decremented according to the sign of the integrator output level. In particular, up/down counter 84 is incremented when the sign of the integrator output level is positive, i.e., the accumulated error is positive. On the other hand, up/down counter 84 is decremented when the sign of the integrator output level is negative, i.e., accumulated error is negative. In one embodiment, up/down counter 84 may be a 9-bit up/down counter with an 8-bit output. This may be due to the slew capability of the overall output response being limited to one DAC value changed per every two clock cycles. Thus, up/down counter 84 may have a programmable mode that will count by either +/−1 (normal) or +/−2 (high slew option) for each comparator output at the loop sampling rate. In other words, during "normal" operation, counter 46 may need to count up or down two values before the DAC output would change, essentially ignoring the LSB of the counter. During "high slew" operation, the 9-bit counter would effectively become an 8-bit counter. The combination of integrator 80 and up/down counter 84 operates as a double integrator that provides ADC 100 with decreased stability. ADC 100 may, however, be made more stable by inserting a digital zero or a pole-zero pair into the transfer function of the feedback loop.

To provide closed loop stability, ADC 100 may include a compensation module 104. Compensation module 104 may compensate for the double integrator phase shift in the feedback loop. Compensation module 104 may introduce a zero to the closed loop transfer function. This compensation technique keeps the design modulating in a controlled state-space so that the quantization noise is most efficiently shaped to frequencies above the signal passband. In one embodiment, an output of comparator 102 may bypass up/down counter 84 and be added to the output of up/down counter 84. In another embodiment, compensation module 104 may add filter zero at $1−0.5*z^{−1}$ or at $z=+\frac{1}{2}$. Although illustrated in FIG. 5 as inserting a zero into the feedback transfer function in the digital domain, similar techniques may be used to insert a pole-zero pair into the feedback transfer function in the analog domain, e.g., between integrator 80 and comparator 102 at outputs 92A and 92B.

ADC 88 includes a negative feedback loop that includes multi-bit DAC 86. The feedback loop continuously cycles in a stable manner integrating the error between input signal 88 and reconstructed signal 96 output by multi-bit DAC 86. The feedback loop drives this integral to zero by cycling the DAC output above and below the input signal. In particular, the feedback loop drives the integration of the error downward towards zero when DAC output 96 is above the input signal 88. Similarly, the feedback loop drive the integration of the error upward towards zero when DAC output 96 is below the input signal 88. Thus, over time the positive and negative DAC feedbacks are forced to balance the integration error (integrated difference) between reconstructed signal 96 and input signal 88.

In one embodiment, multi-bit DAC 86 may comprise a charge redistribution capacitive DAC (CAPDAC). The CAPDAC includes a plurality of capacitors. In one embodiment, the plurality of capacitors may be arranged in two binary weighted CAPDAC arrays; a most significant bit (MSB) array and a least significant bit (LSB array). The CAPDAC arrays may, for example, be partitioned as a 5-bit capacitor array for the MSB array and a 3-bit capacitor array for the LSB array. The 5-bit MSB capacitor array may, for example, include a bank of 31 capacitors and the 3-bit capacitor array may include a bank of 7 capacitors. The two binary weighted arrays may be connected by one inter-stage capacitor (IS). The D/A output voltage can be ideally calculated as:

$$Vdacout = \frac{Vref}{32C}\left[\sum_{i=0}^{4} biCi + \left(\sum_{i=5}^{7} \frac{(biCi)}{8}\right)\right]$$

where bi & Ci are the digital binary and weighted capacitor value of the respective MSB (i=0:4) or LSB (i=5:7) bit. The CAPDAC may be formed in a number of other ways. For example, the CAPDAC may include a number of different split arrays or a different number of bits each of the arrays. Alternatively, CAPDAC may not be a split array, but instead a purely binary weighted array. The CAPDAC described above is described purely as an example of the kind of CAPDAC that may be used in ADC 100.

To improve linearity, noise and resolution of the feedback of multi-bit DAC 86, and hence the overall linearity, noise and resolution ADC 100, multi-bit DAC 86 may include a bit error averaging (BEA) module 106. BEA module 106 may be particularly useful for the capture detection (CD) channel where differential nonlinearity (DNL) error may be more stringent. BEA module 106 may dynamically select which of the capacitors of the MSB array and LSB array to use to represent the bits. For example, BEA module 106 may dynamically select which of the capacitors of the MSB array and LSB array to use to represent the bits, such that the active time of each capacitor is averaged out over time. In one embodiment, BEA module 106 may reselect different active capacitors with every new DAC value. Alternatively, BEA module 106 may select different active capacitors at a slower rate, e.g., every two or three new DAC values. In this manner, the error introduced by the capacitors, e.g., resulting from physical or performance differences between the capacitors is averaged out over time.

As described above, the output of DAC 86 is a reconstructed representation of input signal 88, and is applied to integrator 80 as negative feedback. DAC 86 provides continuous feedback in a stable manner to integrate the error between input signal 88 and reconstructed signal 96. As described herein, the resolution of DAC is higher than the resolution of the quantizer, which, in the example illustrated in FIG. 5 is realized by comparator 102. Thus, in the example illustrated in FIG. 5, the quanitzer is a single bit comparator that drives DAC 86, which is a multi-bit DAC (e.g., a 6-bit, a 7-bit, an 8-bit or 9-bit DAC). In other embodiments, however, the quantizer may be realized by a multi-bit (e.g., 2-bit quantizer) that has a lower resolution than multi-bit DAC 86. As described above, such a configuration provides the benefits of higher resolution DAC feedback.

Digital signal 90 is also output to a processor (e.g., processor 64 of FIG. 3) for use in monitoring a condition of a patient and/or controlling delivery of a therapy to the patient. For example, in the embodiment of IMD 10 illustrated in FIG. 3, the digital signal may be output to processor 64 to determine whether delivery of therapy, such as demand pacing or arrhythmia termination, is necessary. Processor 64 may, for example, analyze the digital signals to determine whether the patient is experiencing an arrhythmia and control therapy delivery module 66 to deliver one or more pulses when an arrhythmia is detected. Accordingly, in exemplary embodiments, processor 64 comprises a DSP.

Before outputting digital signal 90 to the processor, digital filter and downsample module 108 filters and downsamples digital signal 90. This operation increases the effective converter resolution by filtering out the higher frequency quantization noise in the digital data stream. At the same time, module 108 reduces the sample rate of the digital data stream. The structure of digital filter and downsample module 108 may be different depending on the sensed signal for which ADC 100 is used. In the example in which ADC 100 is used to sense atrial and/or ventricular signals, digital filter and downsample module may include (1) a summation filter to average two samples when operating at 32 KHz or a 2× multiplier when operating at 16 KHz, (2) an Infinite Impulse Response (IIR) first order low pass digital filter with corner frequencies of approximately 60 Hz for the atrial channel, and approximately 88 Hz for the left/right ventricle channels; and (3) a SYNC filter summing the signal down to an output sampling rate (e.g., 1 KHz or 256 Hz). Digital filter and downsample module 108 may be slightly different for other sensed signals. For the capture detection (CD) channel, digital filter and downsample module 108 may include a 2nd order IIR filter with 579 Hz bandwidth which combines with a 488 Hz bandwidth of a final output sync filter to give a −3 dB frequency of 399 Hz. Digital filter and downsample module 108 may include a different arrangement of filtering and downsampling techniques than those described above based on the type of signal being sensed and/or the desired output characteristics of the processor. Digital filter and downsample module 108 may use other filtering techniques. For example, digital filter and downsample module 108 may use Finite Impulse Response (FIR) techniques, e.g., sync^2 filter and decimations followed by two stages of half-pass FIR filter and decimator.

After filtering and downsampling the digital signal 90, scale and offset module 109 produces a two's complement output with standard LSB scaling. The output of scale and offset module 109 is then sent to the processor for monitoring the condition of the patient and/or controlling the delivery of therapy to the patient. In the case of demand pacing, as an example, the processor may analyze the digital signal to identify intrinsic depolarizations, e.g., P-waves or R-waves. The processor may identify the intrinsic depolarizations by, for example, comparing digital signal or a first-order derivative of the digital signal to a threshold value. If an intrinsic depolarization is not identified within a predetermined time period, the processor controls therapy delivery circuitry (FIG. 3) to deliver one or more pacing pulses via electrodes 22, 24, 26, 34, 36, 38 and/or 46.

Additionally, in some embodiments IMD 10 provides capture detection. In such embodiments, processor monitors the ECG received via electrodes 92 on or within the housing of the IMD and the CD channel, illustrated in FIGS. 2 and 3, to detect paced depolarizations of the heart during short interval following delivery of a pacing pulse, which indicates that a delivered pacing pulse "captured" the heart. The processor may detect the paced depolarization by, for example, comparing digital signal or a first-order derivative of the digital signal to a threshold value. If the pacing pulse captured the heart, processor may control therapy delivery module to reduce the amplitude of subsequent pacing pulse. If the pacing pulse failed to capture the heart, processor may control therapy delivery module to increase the amplitude of the pacing pulse. In this manner, processor may maintain the pacing pulse amplitude near a minimal value required to capture the heart, thereby conserving power source 72 (FIG. 3).

Furthermore, in some embodiments, IMD 10 acts as a cardioverter or defibrillator. In such embodiments, processor may detect an arrhythmia based on the frequency of intrinsic depolarizations detected within an ECG using the techniques described above. In response to detecting an arrhythmia, processor may control therapy delivery module 66 to deliver a cardioversion or defibrillation pulse via electrodes 22, 24, 26, 34, 36, 38 and/or 46.

Figure 6:
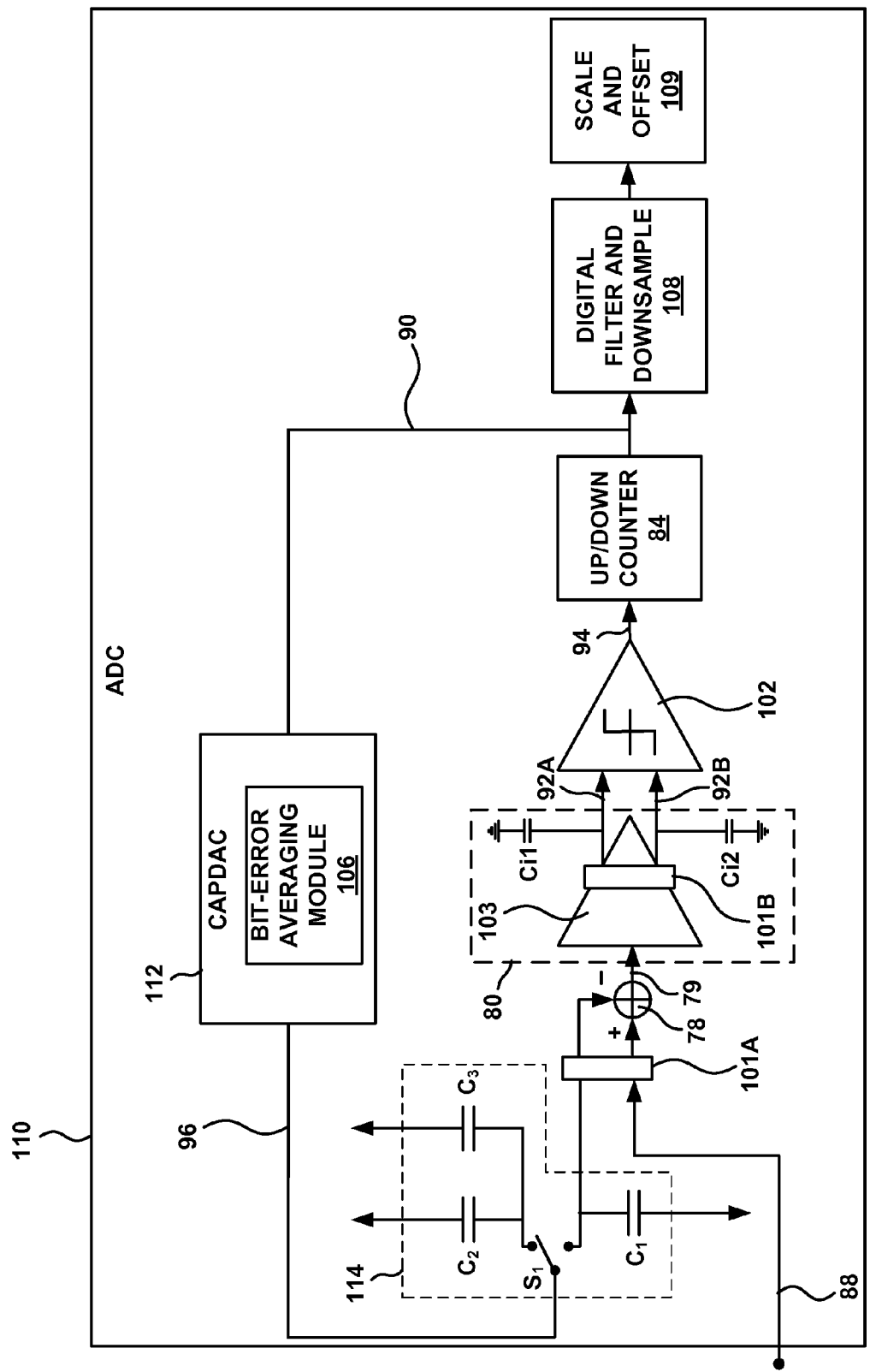
FIG. 6 is a diagram illustrating another example delta-sigma ADC in which a multi-bit capacitive digital-to-analog converter (CAPDAC) is reset in accordance with the techniques of this disclosure.

FIG. 6 is a diagram illustrating another example delta-sigma ADC 110 in which a multi-bit CAPDAC 112 is reset in accordance with the techniques of this disclosure. In particular, CAPDAC 112 is reset such that the affect of the reset on integrator 80 is substantially reduced or eliminated. Operation of delta-sigma ADC 110 is otherwise substantially similar to ADC 100 of FIG. 5.

As described above, CAPDAC 112 includes a plurality of capacitors that may be arranged into one or more capacitor arrays. In one embodiment, the plurality of capacitors may be arranged into two binary weighted CAPDAC arrays; a most significant bit (MSB) array and a least significant bit (LSB) array). The CAPDAC arrays may, for example, be partitioned as a 5-bit MSB array that includes a bank of 31 capacitors, and a 3-bit LSB array that includes a bank of 7 capacitors. However, arrays of different bit partitions and/or different banks of capacitors may be used. The two binary weighted arrays may be connected by one inter-array capacitor (IS).

The CAPDAC output voltage may be approximated using the equation:

$$Vdacout = \frac{Vref}{32C}\left[\sum_{i=0}^{4} biCi + \left(\sum_{i=5}^{7} \frac{(biCi)}{8}\right)\right]$$

where bi and Ci are the digital binary and weighted capacitor value of the respective MSB (i=0:4) or LSB (i=5:7) bit. As described above, the capacitors of the MSB array and LSB array that are used to perform the digital to analog conversion may be rotated to improve linearity, noise and resolution of the feedback of CAPDAC 112. In other words, the combination of capacitors selected in the MSB array and the LSB array is rotated such that the active time of each matches the average, e.g., to within 1%. In this manner, the error introduced by the capacitors is averaged out.

CAPDAC 112 may occasionally be reset for calibration purposes to increase the accuracy of the output of CAPDAC 112. The frequency at which CAPDAC 112 is reset may affect the amount of power consumed by ADC 110 as well as the bit accuracy of the output of CAPDAC. Resetting CAPDAC 112 consumes a portion of the finite power resources of the IMD. Thus, the more frequently CAPDAC 112 is reset the more power is consumed by ADC 110. However, the less frequently CAPDAC 112 is reset the larger the error in the bit accuracy of the output of CAPDAC, e.g., due to loss of capacitive charge due to leakage. In one embodiment, CAPDAC 112 may be reset at a frequency of between 1 kHz and 4 kHz. When the operating frequency of the feedback loop is 16 kHz, for example, CAPDAC 112 may be reset after 16 capacitive redistributions in the case of 1 kHz resetting and after 4 capacitive redistributions in the case of 4 kHz resetting. In these examples the operating frequency ADC 110 is at least four times faster than the rate at which CAPDAC 112 is reset. Resetting CAPDAC 112 at a lower frequency than the operating frequency of the feedback loop may further conserve power resources. However, the conservation of the finite power resources comes at the cost of a slight loss in accuracy. Thus, CAPDAC 112 may be reset at the same frequency as the operating frequency (i.e., clock frequency) in some cases. The rate at which CAPDAC 112 is reset may depend on the size of the capacitors used in CAPDAC 112. Typically larger capacitors require a lower frequency of resets.

CAPDAC 112 may receive a reset signal that activates a reset of CAPDAC 112. The reset signal may, for example, be a clock pulse that is driven at a frequency described above, e.g., 1 kHz or 4 kHz. In response to the reset signal, a switch $S_1$ may switch the output of the CAPDAC 112 from the negative feedback input of integrator 80 to a pseudo load 114. CAPDAC 112 continues to be connected to pseudo load 114 during the reset. Disconnecting CAPDAC 112 from the negative feedback input of integrator 80 allows CAPDAC to be properly reset without affecting the input of integrator 80. Pseudo load 114 mimics the capacitance of the capacitive load of capacitor $C_1$ and integrator 80. In the example illustrated in FIG. 6, pseudo load 114 is made up of capacitor $C_2$ and $C_3$ connected in parallel. Capacitor $C_2$ may be a capacitor of the same size as capacitor $C_1$ and capacitor $C_3$ is approximately the same capacitance as the input of integrator 80. In other embodiments, a different number of capacitors or configurations of capacitors may be used to form pseudo load 114. Connecting CAPDAC 112 to pseudo load 114 ensures that CAPDAC 112 is reset to the reference voltage of ADC 110 (e.g., 1.2V). In other embodiments, CAPDAC 112 may be reset to ground or 0 V.

During resetting of CAPDAC 112, continuous time integrator 80 continues to integrate the difference between input signal 88 and the reconstructed signal 96. If CAPDAC 112 were connected to the negative feedback input of integrator 80 during the reset, the difference would erroneously fluctuate. Thus, ADC 110 includes a sample and hold capacitor $C_1$ coupled to the negative input of integrator 80 to improve the accuracy of the integrated output. Sample and hold capacitor $C_1$ temporarily holds the negative input of integrator 80 at a value approximately equal to a previous, e.g., immediate, value of the output of CAPDAC 112 prior to the reset. In particular, switch $S_1$ is switched away from capacitor $C_1$, leaving the negative input of integrator 80 coupled to the voltage stored on $C_1$. During regular operation $C_1$ is connected through S1 to the output of CAPDAC 112. In one embodiment, sample and hold circuit 114 may hold the negative input of integrator 80 at approximately the last value of the output of CAPDAC 112 for 2 µs using 400 fF capacitor. In this manner, integrator 80 continues to operate unaffected by the capacitor reset.

After resetting CAPDAC 112, the voltage of CAPDAC 112 is redistributed among the plurality of capacitors of CAPDAC 112 to set the output of CAPDAC 112 back to the a previous 8-bit code, e.g., the 8-bit code to which CAPDAC 112 was set immediately before the reset. For example, the reset may occur during the middle of a hold time of up/down counter 84, in which case CAPDAC 112 is set back to the code corresponding with the digital value of up/down counter 84. After the redistribution is performed and CAPDAC 112 settles, switch $S_1$ switches the output of CAPDAC 112 back to the negative input of integrator 80. Integrator 80 may see a small delta in voltage before and after reset due to leakage current on the output of CAPDAC 112 integrated over the time that has passed since the last reset. In the case of 1 kHz reset rate, the small delta in voltage may be integrated over 1 ms. As another example, the small delta voltage may be integrated over 250 µs for a 4 kHz reset rate. With a 27 pF capacitor on the output of CAPDAC with a typical leakage current of 30 pA, the voltage change should be less than 1.1 µV.

Figure 7:
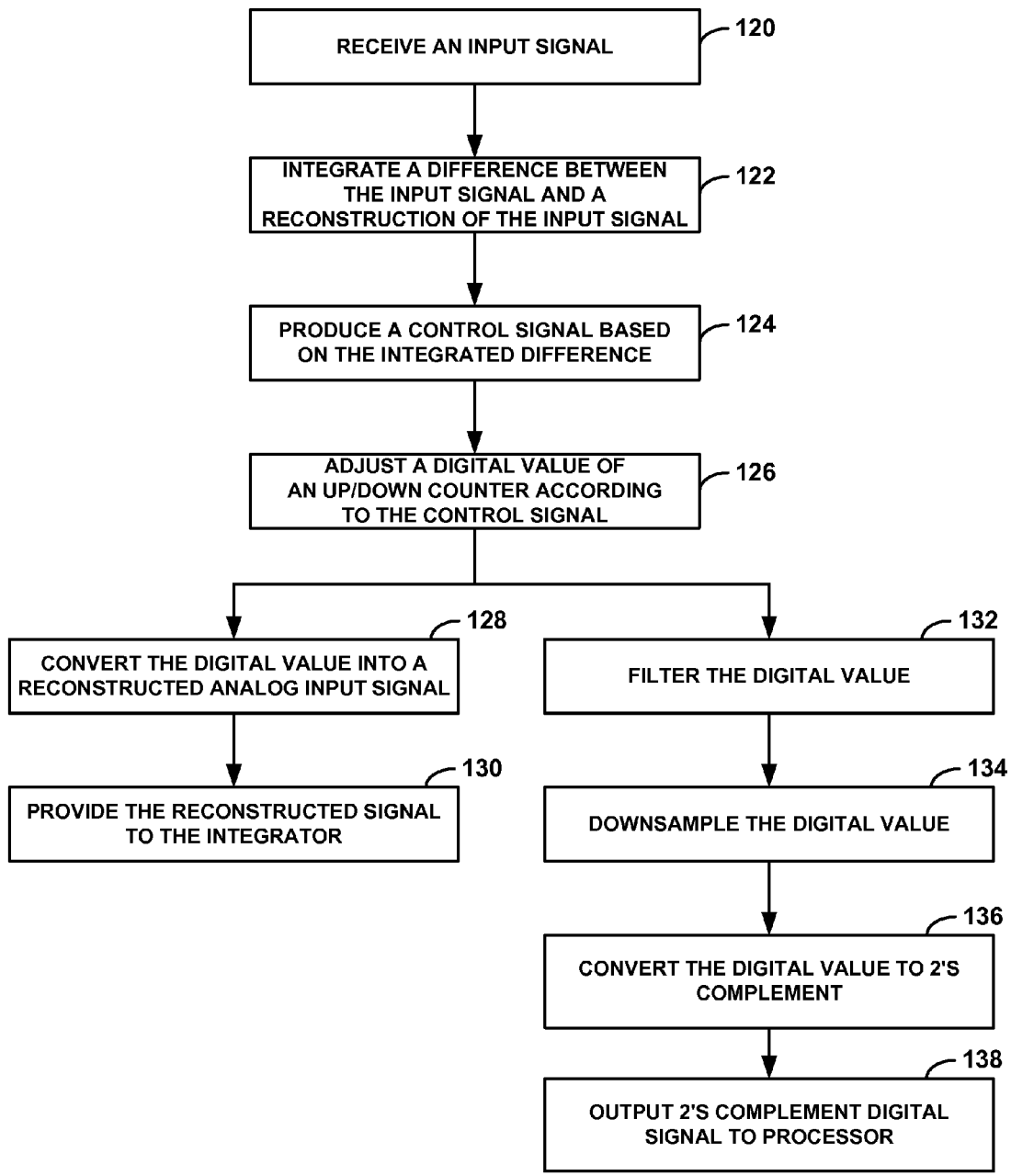
FIG. 7 is a flow diagram illustrating an example operation of a delta-sigma ADC designed in accordance with the techniques of this disclosure.

FIG. 7 is a flow diagram illustrating example operation of a delta-sigma ADC, such as one of ADCs 62 of FIG. 3, designed in accordance with the techniques of this disclosure. ADC 62 receives an analog input signal from at least one sensor (120). In one embodiment, ADC 62 receives an analog input signal that represents a physiological parameter of a patient. ADC 62 integrates a difference between the analog input signal and a reconstructed representation of the analog input signal (122). As will be described in further detail, the reconstructed representation is received at the negative feedback input from a DAC. In one embodiment, ADC 62 may integrate the difference and produce a differential output that has two signals of an equal magnitude, but have opposite polarities (e.g., are 180 degrees out of phase). As described above, differential outputs may provide several advantages ADC produces a control signal based on the integrated difference (124). In one embodiment, ADC 62 includes a comparator 102 that outputs a control signal equal to +1 when the differential signals indicate that the accumulated error is positive, signaling that, on average, the input signal 88 is larger than the reconstructed signal 96. The comparator 102 outputs a control signal equal to −1 (or 0) when the differential signals indicate that the accumulated error is negative, signaling that, on average, the input signal 88 is smaller than the reconstructed signal 96. In this manner, the comparator determines the sign of the output difference, i.e., whether the integrated difference is positive or negative. In other embodiments, ADC 62 may include a multi-bit quantizer that determines not only the sign of the difference, i.e., whether the difference is positive or negative, but also the magnitude of the difference. The higher the resolution of the quantizer, however, the more complex the circuit becomes and the more power that is consumed.

ADC 62 adjusts a digital value of an up/down counter 84 according to the control signal (126). For example, in the case of a 1-bit comparator up/down counter 84 to counts up when the output is a +1 and counts down when the output is a −1 (or 0). The digital value of the up/down counter 84 represents the digital representation of the analog input signal.

ADC 62 includes a multi-bit DAC 86 that generates the reconstructed representation of input signal 88 using the digital value of the up/down counter 84 (128) and provides the reconstructed signal to an integrator (130). DAC 86 provides continuous feedback in a stable manner to integrate the error between input signal and reconstructed signal. In accordance with one aspect of this disclosure, the resolution of the DAC 86 is higher than the resolution of quantizer 82. In one embodiment, for example, the resolution of DAC 86 may include at least four times as many bits as the resolution of the quantizer. For example, the quanitzer may comprise a single bit comparator that drives an up-down counter, which then drives an 8-bit feedback DAC. Such a configuration provides the benefits of higher resolution DAC feedback described above.

ADC 62 may, concurrently with generating and providing the feedback, filter the digital value (132) and downsample the digital value (134) for outputting to a processor 64. Because the feedback loop of ADC 62 may operate at higher frequency than the frequency at which the digital signal is output to the processor, the downsampling may be necessary. In one embodiment, the feedback loop of the ADC may have an operating frequency of 16 kHz or 32 kHz while the frequency at which digital signal is output to the processor may be 1 kHz. In other words, the feedback loop of the ADC integrates the error between input signal 88 and reconstructed signal 96 at approximately 16 or 32 times the rate at which the digital signal is output. Nonetheless, the high resolution feedback provided by the multi-bit DAC may further provide the advantage of a lower oversampling ratio, i.e., lower operating frequency of the feedback loop, relative to embodiments with a lower resolution DAC.

After filtering and downsampling the digital signal 90, ADC 62 may produces a two's complement output with standard LSB scaling (136) and send the two's complement output to the processor for monitoring the condition of the patient and/or controlling the delivery of therapy to the patient (138). In the case of demand pacing, as an example, the processor may analyze the digital signal to identify intrinsic depolarizations and deliver one or more pacing pulses when an intrinsic depolarization is not identified within a predetermined time period.

Figure 8:
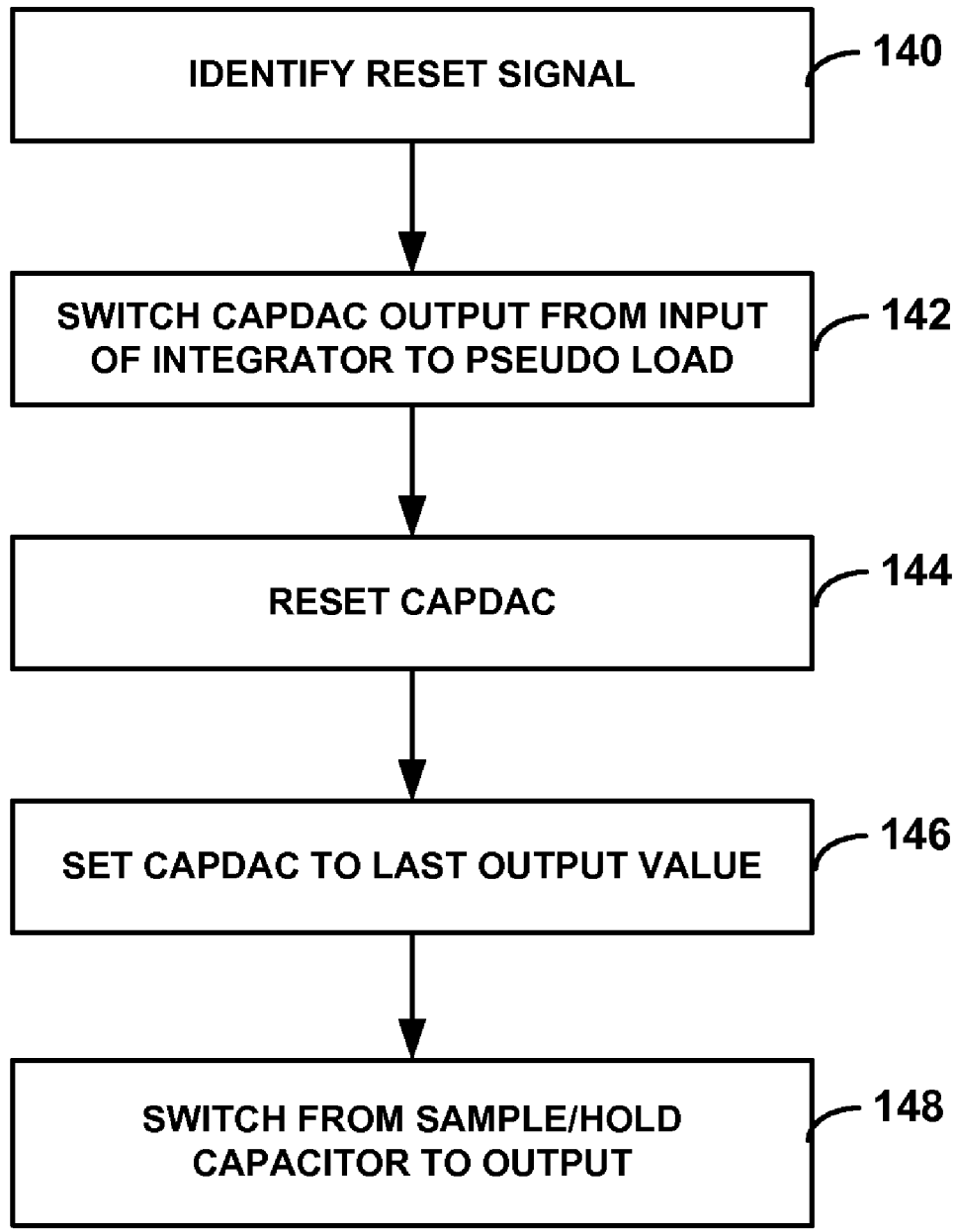
FIG. 8 is a flow diagram illustrating an example operation of an ADC resetting a feedback CAPDAC in accordance with the techniques described herein.

FIG. 8 is a flow diagram illustrating example operation of an ADC, such as one of ADC 110 of FIG. 6, resetting a feedback CAPDAC in accordance with the techniques described herein. ADC 110 receives a reset signal indicating a desire to reset CAPDAC 112 (140). ADC 110 may occasionally be reset for calibration purposes to increase the accuracy of the output of CAPDAC 112. In one embodiment, CAPDAC 112 may be reset at a frequency of between 1 kHz and 4 kHz. When the operating frequency of the feedback loop is 16 kHz, for example, CAPDAC 112 may be reset after 16 capacitive redistributions in the case of 1 kHz resetting and after 4 capacitive redistributions in the case of 4 kHz resetting.

Upon receiving a reset signal, ADC 110 switches the output of CAPDAC 112 from the input of integrator 80 to a pseudo load that mimics the capacitance of $C_1$ and the capacitance of integrator 80 (142). The switch also causes the input integrator 80 input to no longer receive the output of the CAPDAC 112, but instead receive the voltage held on sample and hold capacitor $C_1$. Capacitor $C_1$ thus provides integrator 80 with an input that is approximately equal to the last value of the output of CAPDAC 112.

CAPDAC is reset (144). During resetting of CAPDAC 112, the output of CAPDAC 112 is temporarily connected to a pseudo load such that CAPDAC to be properly reset to a correct common mode voltage (e.g., 1.2V). After resetting CAPDAC 112, the capacitance of CAPDAC 112 is redistributed among the plurality of capacitors of CAPDAC 112 to set the output of CAPDAC 112 back to the last 8-bit code before the reset (146). After the redistribution is performed and settles, the switch $S_1$ switches the output of CAPDAC 112 back to the negative input of integrator 80 (148). In this manner, CAPDAC to be properly reset to a correct common mode voltage (e.g., 1.2V) without affecting the input of integrator 80.

Various embodiments of the invention have been described. However, a person of ordinary skill in the art will recognize that various modifications may be made to the described embodiments without departing from the scope of the claims. For example, although described primarily with reference to first order delta-sigma ADCs, the invention is not so limited. The techniques of this disclosure may be embodied in any higher order delta-sigma ADC. As another example, although described primarily with reference to a cardiac pacemaker, or pacemaker-cardioverter-defibrillator, the invention is not so limited. The invention may be embodied in any implantable medical device, which may deliver any type of therapy, or no therapy.

Furthermore, the invention is not limited to embodiments in which the therapy is controlled based on the digital signal produced by an ADC according to the invention. In some embodiments, the signal is merely analyzed for patient monitoring. Additionally, the invention is not limited to embodiments in which the digital signal is analyzed. In some embodiments, the digital signal produced by an ADC of an IMD according to the invention is stored with the IMD and/or transmitted to another device, e.g., via telemetry.

Moreover, the invention is not limited to embodiments in which the analog input signal is an ECG, or even a signal received via electrodes. In other embodiments, an ADC may receive signals from any type of sensor or transducer. As examples, an ADC may receive an EEG; an electromyogram (EMG); a pressure signal, such as intracardiac, intravascular, or intracranial pressure signal; an impedance signal, which may indicate lead functionality, respiration rate, or pulmonary congestion; a temperature signal; a chemical signal such as glucose concentration or pH; an accelerometer signal that indicates patient motion or position relative to gravity; or a sound signal, which may indicate snoring or apnea. Additionally, an ADC may receive non-physiological signals such as ambient temperature or pressure. Such signals may be received from any electrode, transducer, or sensor known to be able to produce a signal that varies as a function of the above-identified physiological and non-physiological parameters. These and other embodiments are within the scope of the following claims.

The invention claimed is:

1. An implantable medical device comprising:
   at least one sensor that generates an analog input signal;
   at least one delta-sigma analog-to-digital converter (ADC) that converts the analog input signal to a digital signal, the delta-sigma ADC comprising:
      an integrator that produces an integrated difference between the analog input signal and a reconstruction of the analog input signal;
      a quantizer that produces a control signal based on the integrated difference;
      an up/down counter that adjusts a digital value according to the control signal;
      a digital-to-analog converter (DAC) that generates the reconstruction of the analog input signal based on the digital value of the up/down counter and provides the reconstruction of the analog input signal as negative feedback to the integrator, wherein a resolution of the quantizer is less than a resolution of the DAC; and
      a compensation module that compensates for a phase shift in the negative feedback caused by the integrator and the up/down counter,
   wherein the device further comprises:
      a processor that receives the digital signal from the delta-sigma ADC.

2. The device of claim 1, wherein the resolution of the DAC includes at least four times as many bits as the resolution of the quantizer.

3. The device of claim 1, wherein the quantizer comprises a comparator having a 1-bit resolution.

4. The device of claim 3, wherein the DAC has at least a 6-bit resolution.

5. The device of claim 1, wherein the compensation module introduces one of a zero and a pole-zero pair into a transfer function of a feedback loop formed by the DAC in one of an analog domain and a digital domain.

6. The device of claim 1, wherein the integrator comprises a continuous time Gm/C differential integrator that integrates the difference between the analog input signal and the reconstruction of the analog input signal and provides the integrated difference to the quantizer, wherein the quantizer comprises a differential input quantizer.

7. The device of claim 1, wherein the processor controls delivery of a therapy to a patient based on the digital signal from the delta-sigma ADC.

8. The device of claim 7, wherein the processor determines whether an intrinsic depolarization occurs within a time interval based on the digital signal from the delta-sigma ADC and delivers the therapy to the patient based on the determination.

9. The device of claim 1, wherein the sensor generates an analog input signal representative of a sensed physiological parameter of a patient.

10. The device of claim 1, wherein the implantable medical device includes one of a cardiac pacemaker, a cardiac defibrillator, an electrical neurostimulator, an implantable drug delivery device, and a monitoring device.

11. A method comprising:
    receiving an analog input signal from at least one sensor of an implantable medical device;
    converting the analog input signal to a digital signal using at least one delta-sigma analog-to-digital converter (ADC), wherein converting the analog input signal to the digital signal using the at least one delta-sigma ADC comprises:
       producing, with an integrator, an integrated difference between the analog input signal and a reconstruction of the analog input signal,
       producing, with a quantizer, a control signal based on the integrated difference,
       adjusting a digital value of an up/down counter according to the control signal,
       generating the reconstruction of the analog input signal based the digital value of the up/down counter using a digital-to-analog converter (DAC), wherein a resolution of the quantizer is less than a resolution of the DAC,
       providing the reconstruction of the analog input signal as negative feedback to the integrator, and
       compensating for a phase shift in the negative feedback caused by the integrator and the up/down counter,
    wherein the method further comprises:
       sending the digital signal from the delta-sigma ADC to a processor for analysis.

12. The method of claim 11, wherein the resolution of the DAC includes at least four times as many bits the resolution of the quantizer.

13. The method of claim 11, wherein the quantizer comprises a comparator having a 1-bit resolution.

14. The method of claim 13, wherein the DAC has at least a 6-bit resolution.

15. The method of claim 11, wherein compensating for the phase shift comprises introducing at least one of a zero and a pole-zero pair into a transfer function of a feedback loop formed by the DAC in one of an analog domain and a digital domain.

16. The method of claim 11, wherein producing, with the integrator, the integrated difference comprises:
    integrating the difference between the analog input signal and the reconstruction of the analog input signal using a continuous time Gm/C differential integrator; and
    providing the integrated difference to a differential input of the quantizer.

17. The method of claim 11, further comprising controlling delivery of a therapy to a patient based on analysis of the digital signal from the delta-sigma ADC.

18. The method of claim 17, wherein controlling delivery of a therapy to a patient based on analysis of the digital signal comprises:
    determining whether an intrinsic depolarization occurs within a time interval based on the digital signal from the delta-sigma ADC; and
    delivering the therapy to the patient based on the determination.

19. The method of claim 11, wherein receiving an analog input signal from at least one sensor comprises receiving an analog input signal representative of a sensed physiological parameter of a patient.

20. The method of claim 11, wherein the implantable medical device includes one of a cardiac pacemaker, a cardiac defibrillator, an electrical neurostimulator, an implantable drug delivery device, and a monitoring device.

21. An implantable medical device comprising:
  means for generating an analog input signal;
  means for converting the analog input signal to a digital signal, wherein the converting means comprises:
    means for producing an integrated difference between the analog input signal and a reconstruction of the analog input signal,
    means for producing a control signal at a first resolution based on the integrated difference,
    means for adjusting a digital value according to the control signal,
    means for generating the reconstruction of the analog input signal at a second resolution based on the digital value and providing the reconstruction of the analog input signal as negative feedback to the means for producing the integrated difference, wherein the first resolution is less than the second resolution, and
    means for compensating for a phase shift in the negative feedback caused by the means for producing the integrated difference and the means for adjusting the digital value,
  wherein the device further comprises:
    means for analyzing the digital signal from the converting means.

22. The device of claim 21, wherein the second resolution includes at least four times as many bits as the first resolution.

23. The device of claim 22, wherein the first resolution is a 1-bit resolution and the second resolution is at least a 6-bit resolution.

24. The device of claim 21, wherein the means for compensating comprises means for introducing one of a digital zero and a pole-zero pair into a transfer function of a feedback loop formed by the generating means in one of an analog domain and a digital domain.

25. The device of claim 21, wherein the means for producing an integrated difference comprises means for integrating the difference between the analog input signal and the reconstruction of the analog input signal in continuous time, wherein the integrating means outputs an integrated differential signal to a differential input of the quantizer.

* * * * *